United States Patent [19]

Doherty

[11] 4,082,534

[45] Apr. 4, 1978

[54] 1H-IMIDAZO(4,5-b)PYRIDINE DERIVATIVES

[75] Inventor: George O. P. Doherty, Greenfield, Ind.

[73] Assignee: Eli Lilly and Company, Indianapolis, Ind.

[21] Appl. No.: 671,657

[22] Filed: Mar. 29, 1976

Related U.S. Application Data

[60] Division of Ser. No. 447,115, Mar. 1, 1974, Pat. No. 3,961,937, which is a division of Ser. No. 236,195, Mar. 20, 1972, Pat. No. 3,818,022, which is a continuation-in-part of Ser. No. 181,638, Sep. 17, 1971, abandoned, which is a continuation-in-part of Ser. No. 100,410, Dec. 21, 1970, abandoned.

[51] Int. Cl.$^2$ ............................................. A01N 9/22
[52] U.S. Cl. ................................. 71/92; 260/239 A; 260/239 BF; 260/239 E; 260/293.7
[58] Field of Search ............................................. 71/92

[56] References Cited

U.S. PATENT DOCUMENTS

| | | | |
|---|---|---|---|
| 3,448,115 | 6/1969 | Holan et al. | 71/92 |
| 3,561,948 | 2/1971 | Dealtry et al. | 71/92 |
| 3,681,376 | 8/1972 | Scherer et al. | 71/92 |
| 3,813,408 | 5/1974 | Doherty et al. | 71/92 |
| 3,818,009 | 6/1974 | Taylor et al. | 71/92 |

OTHER PUBLICATIONS

Doherty et al., "Herbicidal 1–substituted, etc.", (1971) CA76, No. 85815m (1972).

*Primary Examiner*—Glennon H. Hollrah
*Attorney, Agent, or Firm*—Kathleen R. S. Page; Everet F. Smith

[57] ABSTRACT

Ethers and esters of 1-hydroxy-2-(1,1-difluoroalkyl)-1H-imidazo(4,5-b)pyridine compounds, useful as herbicides.

15 Claims, No Drawings

1H-IMIDAZO(4,5-b)PYRIDINE DERIVATIVES

CROSS-REFERENCE TO RELATED APPLICATIONS

This is a division of my copending application Ser. No. 447,115, filed Mar. 1, 1974 and issued May 8, 1976, as U.S. Pat. No. 3,961,937, which was in turn a division of my then copending application Ser. No. 236,195, filed Mar. 20, 1972, and issued June 18, 1974, as U.S. Pat. No. 3,818,022. Application Ser. No. 236,195 was, in turn, a continuation-in-part of my then copending application Ser. No. 181,638, filed Sept. 17, 1971, and abandoned after the filing of application Ser. No. 236,195. Application Ser. No. 181,638 was, in turn, a continuation-in-part of my then copending application Ser. no. 100,410, filed Dec. 21, 1970, and abandoned after the filing of application Ser. No. 181,638 abandoned.

SUMMARY OF THE INVENTION

The present invention is direction to ethers and esters of 1-hydroxy-2-(1,1-difluoroalkyl)-1H-imidazo(4,5-b)pyridine compounds. These derivatives are of the following formula:

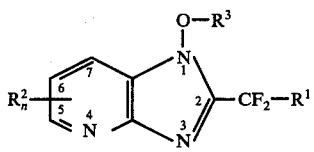

In the above and succeeding formulae throughout the present specification and claims, $R^1$ represents hydrogen, chlorine, fluorine, difluoromethyl, perfluoroalkyl of $C_1$-$C_6$, or radical of the formula

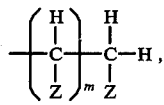

wherein each Z independently represents hydrogen or halogen and m represents 0 or 1; $R^2$ represents amino, halogen, nitro, cyano, loweralkyl of $C_1$-$C_4$, perfluoroalkyl of $C_1$-$C_8$, —$CF_2Cl$, —$CF_2H$, or loweralkylsulfonyl of $C_1$-$C_4$, subject to the limitations (1) that all $R^2$ substituents together contain not more than 8 carbon atoms; (2) that not more than two $R^2$ symbols represent loweralkylsulfonyl groups; and (3) that where two loweralkylsulfonyl groups are present, they are located at the 5- and 7-positions; n represents an integer of from 1 to 3, both inclusive; and $R^3$ represents (1) alkyl of $C_1$-$C_8$;
(2) alkenyl of $C_2$-$C_8$;
(3) cycloalkyl of $C_5$-$C_6$;
(4) benzyl;
(5) phenethyl;
(6) alkanoyl of $C_2$-$C_{16}$;
(7) alkenoyl of $C_3$-$C_{16}$;
(8) carbamoyl of the formula

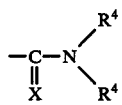

wherein X represents oxygen or sulfur; and one $R^4$ represents phenyl, loweralkyl of $C_1$-$C_4$, or loweralkenyl of $C_2$-$C_4$, and the other $R^4$ represents hydrogen, loweralkyl of $C_1$-$C_4$, or loweralkenyl of $C_2$-$C_4$, subject to the limitation that both $R^4$ moieties taken together do not contain more than six carbon atoms, or both $R^4$ moieties taken together represent straight-chain alkylene of $C_2$-$C_6$, both inclusive;

(9) radical of the formulae

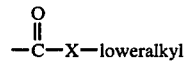

of $C_1$-$C_4$ or

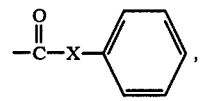

wherein X is, as above, oxygen or sulfur.

(10) radical of the formula

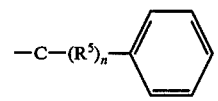

wherein $R^5$ represents methylene, ethylene, or vinylene, and n represents 0 or 1;

(11) radical of the formulae

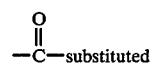

phenyl and

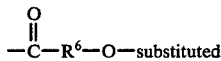

phenyl, wherein substituted phenyl is a phenyl radical bearing from 1-3 substituents, each or which is independently amino, nitro, chloro, methyl, or methoxy, and $R^6$ represents loweralkylene of $C_1$-$C_4$, both inclusive;

(12) —$SO_2$—$R^7$ wherein $R^7$ is loweralkyl as above defined, cycloalkyl of $C_5$-$C_6$, phenyl, substituted phenyl as above defined, or benzyl;

(13) tetrahydro-2-pyranyl.

The compounds so defined are useful as herbicides. In addition, they can be used as starting materials for a process which results in rearrangement or reduction depending on the reaction conditions employed.

DETAILED DESCRIPTION OF THE INVENTION

In the present specification and claims, the term "halogen" is employed to designate bromine, chlorine, fluorine, and iodine, only. In the case of the loweralkyl, loweralkenyl, alkyl, alkenyl, alkanoyl, alkenoyl, and loweralkylene radicals, such radical can be branched or straight-chain.

An essential and distinguishing structural feature of the compounds of the present invention is the substituent at the 2-position (—$CF_2$—$R^1$); representative such radicals include the following:

difluoromethyl
trifluoromethyl
difluorochloromethyl
pentafluoroethyl
heptafluoro-n-propyl
1,1-difluoroethyl
1,1-difluoro-n-propyl
1,1-difluoro-2-bromoethyl
1,1-difluoro-2-chloroethyl
1,1-difluoro-2,3-dichloro-n-propyl
1,1-difluoro-3-bromo-n-propyl
1,1,2-trifluoroethyl
1,1,2-trifluoro-n-propyl
1,1,2,3-tetrafluoro-n-propyl
1,1-difluoro-2-bromo-3-chloro-n-propyl
perfluoro-n-butyl
perfluoro-n-pentyl
perfluoro-n-hexyl
1,1,2,2-tetrafluoroethyl Preferred groups are trifluoromethyl, difluoromethyl, difluorochloromethyl, 1,1,2,2-tetrafluoroethyl, and pentafluoroethyl.

The compounds of the present invention are typically crystalline solids. They are prepared in standard procedures for the derivatization of hydroxy groups. Hence, those of the derivatives claimed herein which are ethers can be prepared by those procedures discussed in chapter 6 of *Synthetic Organic Chemistry*, by Wagner and Zook (John Wiley and Sons, Inc., New York, 1965). The same reference discusses various synthetic procedures which can be employed for the synthesis of those derivatives claimed herein which are carboxylic acid esters (chapter 14), carbamic acid esters (chapter 23), and sulfonic acid esters (chapter 37).

Generally, the compounds of the present invention are conveniently prepared by the reaction of the corresponding 1-hydroxy compounds:

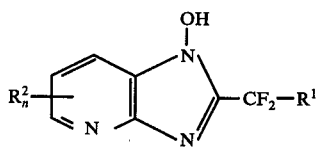

with a halide of the formula R³-X, where X is halo, in the presence of an alkali metal carbonate or other hydrogen halide acceptor. An inert liquid reaction medium can be used. The reaction proceeds under a wide range of temperatures, but is preferably conducted at temperatures of from −20° C. to the reflux temperature. Separation, and if desired, purification, are carried out in conventional procedures.

While the foregoing is the most general method, other methods are convenient and may be preferred for some of the compounds. Thus, those carbamates of the formula

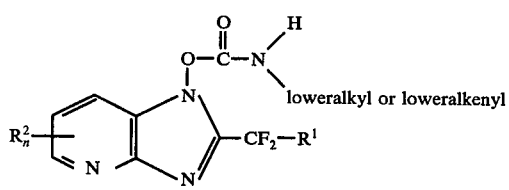

are more readily prepared by reacting the corresponding 1-hydroxy-1H-imidazo(4,5-b)pyridine with an isocyanate of the formula

O=N=C=loweralkyl or loweralkenyl

The reaction is conducted in conventional procedures.

Likewise, the carboxylic ester compounds of the present invention other than the carbamate esters are often preferably prepared by reacting the desired carboxylic acid as its anhydride with the corresponding 1-hydroxy-1H-imidazo(4,5-b)pyridine starting compound. Furthermore, in the case of the present compounds which are ethers, preparation is sometimes preferably carried out by reaction of the 1-hydroxy-1H-imidazo(4,5-b)pyridine with an olefin; this is particularly preferred in the case of the tetrahydro-2-pyranyl ether. The alkenyl ethers may also be preferably prepared by addition to an alkyne.

Yet other synthetic techniques can be used in the preparation of the compounds of the present invention; examples are the use of N,N'-carbonyldiimidazole or N,N'-dicyclohexyldicarbodiimide (See *Reagents for Organic Synthesis*, Fieser and Fieser (John Wiley and Sons, 1967), pages 114 et seq. and 231 et seq., respectively.

The following examples illustrate the present invention and will enable those skilled in the art to practice the same.

EXAMPLE 1

1-METHOXY-6-CHLORO-2-(TRIFLUOROMETHYL)-1H-IMIDAZO(4,5-b)PYRIDINE

1-Hydroxy-6-chloro-2-(trifluoromethyl)-1H-imidazo-(4,5-b)pyridine (5 grams), 80 milliliters of acetone, 5 milliliters of methyl iodide, and 10 grams of anhydrous potassium carbonate were mixed, heated and refluxed with stirring for twelve hours. The reaction mixture was then filtered, evaporated and eluted off of a silica column with diethyl ether, yielding the desired 1-methoxy-6-chloro-2-(trifluoromethyl)-1H-imidazo(4,5-b)pyridine product. It was recrystallized from petroleum ether (boiling at 60°–80° C.). The product so obtained melted at 91°–2° C.

Analysis, Calc.: C, 38.20; H, 1.99; N, 16.70. Found: C, 37.92; H, 2.32; N, 16.75.

EXAMPLE 2

1-BENZYLOXY-6-CHLORO-2-(TRIFLUOROMETHYL)-1H-IMIDAZO(4,5-b)PYRIDINE

1-Hydroxy-6-chloro-2-(trifluoromethyl)-1H-imidazo-(4,5-b)pyridine (5 grams), 10 milliliters of benzyl bromide, 20 grams of anhydrous potassium carbonate, and 100 milliliters of ethanol were mixed, heated to reflux, and refluxed for one hour. The reaction mixture was then filtered, evaporated under vacuum, and extracted with diethyl ether. The extract was filtered and evaporated under vacuum yielding a dark oil which on standing crystallized as the desired 1-benzyloxy-6-chloro-2-(trifluoromethyl)-1H-imidazo(4,5-b)pyridine. It was recrystallized from a mixture of acetone and petroleum ether boiling at 60°–80° C., m.p., 107°–09° C.

Analysis, Calc.: C, 51.31; H, 2.77; N, 12.82. Found: C, 51.54, H, 2.62; N, 13.12.

EXAMPLE 3

1-ACETOXY-6-CHLORO-2-(TRIFLUOROMETHYL)-1H-IMIDAZO(4,5-b)PYRIDINE

1-Hydroxy-6-chloro-2-(trifluoromethyl)-1H-Imidazo(4,5-b)pyridine (5 grams), 25 milliliters of acetic anhydride and 0.1 milliliter of sulfuric acid were mixed with stirring at 25° C. for fifteen minutes. The reaction mixture was then heated to reflux and refluxed for one-half hour, poured into ice with stirring, stirred for ten minutes and filtered. Filtration yielded the desired 1-acetoxy-6-chloro-2-(trifluoromethyl)-1H-imidazo(4,5-b)pyridine product as a solid. It was taken up in ether, dried over magnesium sulfate, and the ether evaporated. The product then melted at 103°–04° C.

Analysis, Calc.: C, 38.65; H, 1.80; N, 15.02. Found: C, 38.88; H, 1.92; N, 15.02.

EXAMPLE 4

1-OCTANOYLOXY-6-CHLORO-2-(TRIFLUOROMETHYL)1H-IMIDAZO(4,5-b)PYRIDINE

To 1-hydroxy-6-chloro-2-(trifluoromethyl)-1H-Imidazo(4,5-b)pyridine (2.37 grams) in 5 milliliters of pyridine was added octanoyl chloride (1.63 grams). The addition was carried out portionwise with stirring and resulted in the precipitation of a white solid. The reaction mixture was set on a steam bath for twenty minutes, then poured over ice cold aqueous HCl. An oil separated and subsequently crystallized on vigorous stirring. This precipitate was removed by filtration, dissolved in ether, dried over magnesium sulfate, filtered, and ether removed by evaporation under vacuum. The substance was purified by distillation, m.p., 33.5°–35.5° C.

Analysis, Calc.: C, 49.52; H, 4.71; N, 11.55. Found: C, 49.81; H, 4.93; N, 11.29.

EXAMPLE 5

1-(ALLYLCARBAMOYLOXY)-6-CHLORO-2-(TRIFLUOROMETHYL)-1H-IMIDAZO(4,5-b)PYRIDINE

1-Hydroxy-6-chloro-2-(trifluoromethyl)-1H-imidazo(4,5-b)pyridine (4.6 grams) was dissolved in 10 milliliters of diethyl ether and 2.4 milliliters of allyl isocyanate added and the reaction mixture stirred at room temperature for thirty-six hours. The reaction mixture was then filtered yielding 4.75 grams of a white powder, the desired 1-(allylcarbamoyloxy)-6-chloro-2-(trifluoromethyl)-1H-imidazo(4,5-b)pyridine. An additional portion of the product was obtained by evaporating the filtrate. The combined products were recrystallized from a mixture of diethyl ether and petroleum ether boiling at 60°–80° C., m.p., about 210° C.

Analysis, Calc.: C, 41.20; H, 2.51; N, 17.47. Found: C, 41.42; H, 2.51; N, 17.25.

EXAMPLE 6

1-(METHYLSULFONYLOXY)-6-CHLORO-2-(TRIFLUOROMETHYL)-1H-IMIDAZO(4,5-b)PYRIDINE

1-Hydroxy-6-chloro-2-(trifluoromethyl)-1H-imidazo-(4,5-b)pyridine (5 grams) in 15 milliliters of pyridine was cooled to 5° C. with stirring and methylsulfonyl chloride (5 milliliters) was added in 1-milliliter portions, maintaining the temperature at about 5° C. After the addition was completed, the reaction mixture was stirred for two hours at 5°–10° C., then poured into 30 grams of ice and 20 milliliters of concentrated hydrochloric acid. The desired 1-(methylsulfonyloxy)-6-chloro-2-(trifluoromethyl)-1H-imidazo(4,5-b)pyridine product precipitated and was separated by filtration and washed with water. The washed product was taken up in diethyl ether with a trace of acetone, dried over magnesium sulfate and the solvent evaporated under vacuum. The product so obtained melted at 136.7° C.

Analysis, Calc.: C, 30.44; H, 1.60; N, 13.31. Found: C, 30.48; H, 1.83; N, 13.00.

EXAMPLE 7

1-METHOXY-6-AMINO-5,7-DIBROMO-2-(TRIFLUOROMETHYL)-1H-IMIDAZO(4,5-b)PYRIDINE

6-Amino-5,7-dibromo-2-trifluoromethyl-1-hydroxy-1H-imidazo(4,5-b)pyridine (1 gram) was mixed and stirred for two hours with 2 milliliters of methyl iodide, 2 grams of potassium carbonate, and 10 milliliters of acetone. The reaction mixture was then diluted with about 80 milliliters of ether and washed with five 15-milliliter portions of water. The ether layer was dried over magnesium sulfate and filtered with carbon, and the ether removed on a rotary evaporator. The resulting 1-methoxy-6-amino-5,7-dibromo-2-(trifluoromethyl)-1H-imidazo(4,5-b)pyridine product melted at 169°–72° C. A portion was recrystallized from methanol, m.p., 177°–8° C.

Analysis, Calc.: C, 24.64; H, 1.29; N, 14.37. Found: C, 24.96; H, 1.51; N, 14.48.

EXAMPLE 8

1-(METHYLCARBAMOYLOXY)-6-CHLORO-5,7-DIBROMO-2-(TRIFLUOROMETHYL)-1H-IMIDAZO(4,5-b)PYRIDINE

6-Chloro-5,7-dibromo-1-hydroxy-2-(trifluoromethyl)-1H-imidazo(4,5-b)pyridine (0.9 gram) was mixed with ether (15 milliliters) and methyl isocyanate (2 milliliters) and stirred for fifteen minutes. Triethylamine (0.01 milliliter) was added, and the solution became homogenous. It was permitted to stand for sixteen hours, diluted with 50 milliliters diethyl ether; washed with 0.5N HCl, water, and saturated NaCl; then dried over magnesium sulfate, and evaporated. The resulting 1-(methylcarbamoyloxy)-6-chloro-5,7-dibromo-2-(trifluoromethyl)-1H-imidazo(4,5-b)pyridine product was recrystallized from chloroform, m.p., 216° C.

Analysis, Calc.: C, 23.89; H, 0.89; N, 12.38. Found: C, 23.82; H, 0.90; N, 12.16.

EXAMPLES 9–61

Other representative compounds of the present invention, prepared in accordance with the foregoing teachings, include the following:

1-allyloxy-6-chloro-2-(trifluoromethyl)-1H-imidazo(4,5-b)pyridine, $n_D^{23.5}$ 1.5204.

1-isopropoxy-6-chloro-2-(trifluoromethyl)-1H-imidazo(4,5-b)-pyridine, m.p., 49°–51° C.

1-ethoxy-6-chloro-2-(trifluoromethyl)-1H-imidazo(4,5-b)pyridine, $n_D^{25}$ 1.5082.

1-(methylcarbamoyloxy)-6-chloro-2-(trifluoromethyl)-1H-imidazo(4,5-b)pyridine, m.p., 267° C.

1-(2-methoxy-3,6-dichlorobenzoyloxy)-6-chloro-2-(trifluoromethyl) -1H-imidazo(4,5-b)pyridine, m.p., 148°–9° C.

1-ethoxy-2,6-bis(trifluoromethyl)-1H-imidazo(4,5-b)-pyridine, $n_D^{25}$ 1.5100.

1-methoxy-6-nitro-2-(trifluoromethyl)-1H-imidazo(4,5-b)-pyridine.

1-n-octyloxy-6-(methylsulfonyl)-2-(heptafluoro-n-propyl)-1H-imidazo(4,5-b)pyridine.
1-n-butoxy-6-fluoro-2-(1,1-difluoroethyl)-1H-imidazo(4,5-b)-pyridine.
1-phenethoxy-2,6-bis(chlorodifluoromethyl)-1H-imidazo(4,5-b)-pyridine.
1-vinyloxy-2,6-bis(difluoromethyl)-1H-imidazo(4,5-b)pyridine.
1-(dimethylcarbamoyloxy)-6-bromo-2-(perfluoro-n-hexyl)-1H-imidazo(4,5-b)pyridine.
1-methacryloyloxy-6-chloro-2-(trifluoromethyl)-1H-imidazo-(4,5-b)-pyridine.
1-lauroyloxy-2,6-bis(trifluoromethyl)-1H-imidazo(4,5-b)pyridine.
1-(2,4-dichlorophenoxyacetoxy)-6-chloro-2-(trifluoromethyl)-1H-imidazo(4,5-b)pyridine.
1-benzoyloxy-2,6-bis(trifluoromethyl)-1H-imidazo(4,5-b)pyridine.
1-(phenylacetoxy)-6-chloro-2-(trifluoromethyl)-1H-imidazo-(4,5-b)-pyridine.
1-(3-phenylpropionyloxy)-6-(methylsulfonyl)-1H-imidazo-(4,5-b)-pyridine.
1-cinnamoyloxy-6-chloro-2-(trifluoromethyl)-1H-imidazo(4,5-b)-pyridine.
1-(3-(2,4,5-trichlorophenoxy)propionyloxy)-6-chloro-2-(trifluoromethyl)-1H-imidazo(4,5-b)pyridine.
1-cyclohexyloxy-6-chloro-2-(trifluoromethyl)-1H-imidazo-(4,5-b)-pyridine.
1-(phenylsulfonyloxy)-2,6-bis(difluoromethyl)-1H-imidazo(4,5-b)-pyridine.
1-(benzylsulfonyloxy)-6-chloro-2-(difluoromethyl)-1H-imidazo-(4,5-b)-pyridine.
1-(cyclohexylsulfonyloxy)-6-nitro-2-(trifluoromethyl)-1H-imidazo(4,5-b)-pyridine.
1-((p-chlorophenyl)sulfonyloxy)-6-chloro-2-(trifluoromethyl)-1H-imidazo(4,5-b)-pyridine.
1-(2-butenyloxy)-6-(isopropylsulfonyl)-2-(1,1-difluoro-3-chloropropyl)-1H-imidazo(4,5-b)-pyridine.
1-(6-octenyloxy)-6-chloro-2-(trifluoromethyl)-1H-imidazo-(4,5-b)-pyridine.
1-(9-hexadecenoyloxy)-6-chloro-2-(trifluoromethyl)-1H-imidazo-(4,5-b)-pyridine.
1-(isopropylthiocarbamoyloxy)-6-chloro-2-(pentafluoroethyl)-1H-imidazo(4,5-b)pyridine.
1-(3-amino-2,5-dichlorobenzoyloxy)-6-chloro-2-(trifluoromethyl)-1H-imidazo(4,5-b)pyridine.
1-(2,5-dichloro-3-nitrobenzoyloxy)-6-chloro-2-(trifluoromethyl)-1H-imidazo(4,5-b)pyridine.
1-(2-(4-chloro-o-tolyloxy)acetoxy)-2,6-bis(trifluoromethyl)-1H-imidazo(4,5-b)pyridine.
1-(tetrahydro-2-pyranyloxy)-6-chloro-2-(trifluoromethyl)-1H-imidazo(4,5-b)pyridine.
1-methoxy-2,6-bis(trifluoromethyl)-1H-imidazo(4,5-b)pyridine.
1-(methylcarbamoyloxy)-2,6-bis(trifluoromethyl)-1H-imidazo-(4,5-b)pyridine.
1-(2-methoxy-3,6-dichlorobenzoyloxy)-6-amino-2-(trifluoromethyl)-1H-imidazo(4,5-b)pyridine.
1-(methylsulfonyloxy)-6-nitro-5,7-dibromo-2-(trifluoromethyl)-1H-imidazo(4,5-b)pyridine.
1-(2-(4-chloro-o-tolyloxy)acetoxy)-5-chloro-2-(trifluoromethyl)-1H-imidazo(4,5-b)pyridine.
1-(2,4-dichlorophenoxyacetoxy)-7-chloro-2-(trifluoromethyl)-1H-imidazo(4,5-b)pyridine.
1-methoxy-5-(methylsulfonyl)-2-(pentafluoroethyl)-1H-imidazo-(4,5-b)pyridine.
1-ethoxy-7-fluoro-2-(difluoromethyl)-1H-imidazo(4,5-b)pyridine.
1-propionyloxy-5-chloro-6-bromo-2-(1,1,2,2-tetrafluoroethyl)-1H-imidazo(4,5-b)pyridine.
1-octanoyloxy-7-amino-2-(difluorochloromethyl)-1H-imidazo(4,5-b)-pyridine.
1-methoxy-7-nitro-2-(difluorochloromethyl)-1H-imidazo(4,5-b)-pyridine.
1-allyloxy-2,7-bis(trifluoromethyl)-1H-imidazo(4,5-b)pyridine.
1-cyclohexyloxy-5,6,7-trinitro-2-(trifluoromethyl)-1H-imidazo-(4,5-b)pyridine.
1-benzyloxy-5,6,7-trichloro-2-(difluoromethyl)-1H-imidazo(4,5-b)-pyridine.
1-phenethoxy-5,6-bis(difluoromethyl)-2-(trifluoromethyl)-1H-imidazo(4,5-b)pyridine.
1-acetoxy-2,5,6-tris(trifluoromethyl)-1H-imidazo(4,5-b)pyridine.
1-acryloyloxy-5,6-bis(difluorochloromethyl)-1H-imidazo(4,5-b)pyridine.
1-(tetrahydro-2-pyranyloxy)-5,6-bis(ethylsulfonyl)-2-(trifluoromethyl)-1H-imidazo(4,5-b)pyridine.
1-benzoyloxy-6-methyl-2-(trifluoromethyl)-1H-imidazo(4,5-b)pyridine.
1-methoxy-6-(perfluorooctyl)-2-(trifluoromethyl)-1H-imidazo(4,5-b)-pyridine.

The compounds of the present invention are adapted to be employed as herbicides. The compounds can be utilized to achieve broad herbicidal action; hence, in its broadest sense, the present invention is directed to a method which comprises applying to a plant part, which can be a stem, leaf, flower, fruit, root, or seed or other similar reproductive unit of a plant, a growth-inhibiting amount of one of the compounds of the present invention. However, the compounds can also be utilized to take advantage of selective patterns of herbicidal activity.

It is not critical to the practice of the present invention that complete destruction of undesirable vegetation be obtained, it being adequate if the growth of the unwanted vegetation is merely inhibited. Especially where selective action is sought, inhibition falling short of actual killing is adequate, particularly when combined with naturally occurring conditions such as limited moisture and the like which more adversely affect the vegetation selectively inhibited than the crop plant.

The compounds of the present invention are suited to a wide variety of herbicidal applications. Thus, for example, at rates which evoke the selective action of the compounds, which rates are defined more completely hereinbelow, the compounds can be used as selective herbicides in crop plants, such as, for example, cotton, corn, sorghum, soybeans, and the like. In such use, application can be made preemergent to both crops and weeds, or, preferably by means of a directed spray application technique postemergent to the crop plant but both preemergent and postemergent to the weeds. In another application, the compounds can be used to give broad herbicidal action on non-crop land, including intermittently non-crop strips of contour-farmed land. For such usage on so-called fallow land, application can be made in spring to suppress vegetative growth until a fall or following spring planting, or in the fall to suppress vegetative growth until a spring or following fall planting. Furthermore, in another application, the present compounds can be utilized to control weeds in tree crop plantings, such as plantings of the various citrus trees. In all of these various applications, and yet others for which the present compounds are suited, another advantage is that the compounds need not be disced into the soil being treated, it being adequate if one of the compounds, or a formulation containing one of the compounds, is merely spread onto the top surface. However, where desired or convenient, the compounds can be disced into, or otherwise mechanically mixed with the soil. In addition to the foregoing terrestrial embodiments, the present compounds can also be utilized as aquatic herbicides.

The practice of the present invention in any of its numerous embodiments can in some instances be carried out with unmodified compound; however, for good results, it is generally necessary that the compound be employed in modified form, that is, as one component of a composition formulated to implement the plant growth-inhibiting effects. Thus, for example, the active agent can be mixed with water or other liquid or liquids, preferably aided by the usage of a surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulations are known in the art and can be employed in implementing the present invention.

In carrying out the novel method of the present invention, the exact amount of the active agent employed is not critical and will vary, depending upon the type of growth-inhibiting effect desired, the identity of the plants concerned, the particular active agent used, weather conditions, and the like. In general, a broad growth-inhibiting effect is obtained with rates of from 3-5 to 20 pounds or more of active agent per acre, and such rates are suitable and effective for control of vegetative growth on fallow land. When it is desired to obtain a selective growth-inhibiting effect on weeds in areas containing crop plants such as corn, soybeans, and cotton, rates of from 0.25 or less to 5 pounds generally give good results. When in the typical mode of operation, the active agent is employed as a composition comprising the agent, the exact concentration of active agent in the composition is not critical, except that the concentration and total amount of formulation employed be adequate to supply the appropriate amount of active agent on a per acre basis. In general, good results are obtained when employing formulations containing the active agent in a concentration of from 0.5 to 10 percent or higher, in the instance of a liquid formulation; and in a concentration of from 1.0 to 5.0 percent or higher, in the instance of a dust, powder, granule, or the like. More concentrated formulations can be prepared and are often preferred in that they can serve, depending upon the particular application contemplated and the particular concentration, both as a concentrated formulation for purposes of shipment, storage, and the like, and as an ultimate treating composition. Thus, for example, formulations often preferably contain a surface active agent and the present active agent, the latter being present in an amount of from 0.5 to 99.5 percent, by weight; or an inert, finely divided solid and the present active agent, the latter being present in an amount of from 1.0 to 99.0 percent, by weight. Such formulations, as indicated, can be employed directly in certain applications, but can also be diluted and subsequently employed in many other applications.

Liquid compositions containing the desired amount of active agent are prepared by dissolving the substance in a liquid with or without the aid of a surface active dispersing agent such as, an ionic or non-ionic emulsifying agent. Most preferably, the subject compound is dissolved in water or in an organic liquid carrier, aided by the use of a surface active dispersing agent. Suitable such organic liquid carriers include agricultural spray oils and the petroleum distillates such as diesel fuel, kerosene, fuel oil naphthas and Stoddard solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. Representative surface active agents which are suitably employed in implementing the present invention are identified in U.S. Pat. Nos. 3,095,299, second column, lines 25-36, 2,655,447, column 5, and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified by incorporation therein of an effective amount of a surfactant which facilitates the dispersion and spreading of the formulation of the plant leaf surfaces and the incorporation of the formulation by the plant.

In accordance with the present invention, the active agent can be dispersed in soil or other growth media in any convenient fashion. Applications can be carried out by simply mixing with the media, by applying to the surface of soil and thereafter dragging or discing into the soil to the desired depth, or by employing a liquid carrier to accomplish the penetration and impregnation. The application of spray and dust compositions to the surface of soil, or to plant parts or the above ground surfaces of plants can be carried out by conventional methods, e.g., power dusters, boom and hand sprayers and spray dusters, whether surface or air-borne. However, while such conventional modes of application can be used, they are not required. As above noted, it is an advantage of the present invention that the compounds serving as active agent are active and effective as herbicides when merely placed on the surface of the soil, without any additional step to assist incorporation. Thus, the compounds are of substantially the same efficacy regardless of whether they are applied to the surface only, or whether they are applied to the surface and subsequently disced into the soil.

In a further method, the distribution of the active agent in soil can be accomplished by introducing the agent into the water employed to irrigate the soil. In such procedures, the amount of water is varied with the porosity and water holding capacity of the soil to obtain a desired depth of distribution of the agent.

In addition, the present invention method also comprehends the employment of an aerosol composition containing one or more of the present active agents as an active compound. Such a composition is prepared according to conventional methods wherein the agent is dispersed in a solvent, and the resultant dispersion mixed with a propellant in liquid state. Such variables as the particular agent to be used and the nature of the vegetation which is to be treated will determine the desirability of the solvent and concentration of the agent therein.

Satisfactory results are obtained when the active agent of the present invention, or a composition comprising such active agent, is combined with other agricultural materials intended to be applied to plants, plant parts, or their habitats. Such materials include fertilizers, fungicides, nematocides, insecticides, other herbicides, soil conditioning agents, and the like.

The following further examples illustrate the herbicidal utility of the compounds of the present invention.

EXAMPLES 62–70

Various of the compounds of the present invention were evaluated for preemergent application to various crop and weed species. Each compound was formulated by dissolving it in a 1:1 mixture of acetone and ethanol containing a small amount of a blend of sulfonate nonionic emulsifying agents; the solution was then diluted first with deionized water, then serially with deionized water containing 1000 ppm. of the blend of emulsifiers. The resulting solutions contained the subject compound in various amounts, the emulsifier blend in a concentration of 0.1 percent, and the acetone and ethanol each in a concentration of 4.0 percent.

A soil was prepared consisting of one part masonry sand and one part shredded top soil blended together in a cement mixer. One gallon of this soil was placed in a 21.5 × 31.5 cm. galvanized flat and was patted down with a bench brush until level. A three-row marker was used to make 2 ½ cm. deep furrows in approximately two-fifths of the flat. Crop seeds consisting of four kernels of corn, five cotton seeds and five soybean seeds were placed in these furrows. A four-row template was then placed on the remaining soil and the indicated approximate numbers of each of the following seeds were planted, one species to each section: foxtail (millet), 80–100 seeds; velvetleaf (40–50 seeds); rough pigweed (150–250 seeds); and large crabgrass (100–150 seeds).

Sufficient soil was added to cover the entire flat. Thus, the weed seeds were covered to a depth of about 6 mm. and the crop seeds were covered to a depth of about 3 cm.

In assaying the effect of the composition as preemergent herbicides, a flat prepared as above, taken either on the day of planting or on the next day, was placed in a chamber equipped with a turntable and an air exhaust. The herbicidal composition was applied to the flat with a modified DeVilbiss atomizer hooked to an air source. Twelve and one-half milliliters of the composition under test were applied to each flat either on the day of planting or on the succeeding day. Injury ratings and observations as to type of injury were made eleven to twelve days after treatment. The injury rating scale used was as follows:

0—no injury
1—slight injury
2—moderate injury
3—severe injury
4—death

When more than one determination was carried out at a given rate, an average value was calculated for the injury rating.

In the following table setting forth the results of the evaluation, column 1 gives the name of the compound under test; column 2, the rate in pounds per acres at which the compound was applied to the test flat; and the remaining columns, the injury to the particular plant seeds or seedlings as measured by the foregoing scale.

TABLE I

| Compound | Lbs./Acre | Corn | Cotton | Soybean | Crabgrass | Pigweed | Foxtail | Velvetleaf |
|---|---|---|---|---|---|---|---|---|
| 1-Methoxy-6-chloro-2-(trifluoromethyl)-1H-imidazo(4,5-b)pyridine | 8 | 2 | 4 | 3 | 3 | 3 | 4 | 3 |
|  | 4 | 2 | 2 | 1 | 4 | 4 | 4 | 4 |
|  | 2 | 1 | 1 | 1 | 4 | 3 | 4 | 4 |
|  | 1 | 0 | 1 | 0 | 3 | 3 | 3 | 4 |
| 1-Acetoxy-6-chloro-2-(trifluoromethyl)-1H-imidazo(4,5-b)pyridine | 8 | 1 | — | — | 3 | 2 | 3 | 3 |
|  | 4 | 1 | 0 | 0 | 2 | 2 | 3 | 3 |
|  | 2 | 0 | 0 | 1 | 1 | 2 | 3 | 3 |
| 1-Ethoxy-6-chloro-2-(trifluoromethyl)-imidazo(4,5-b)pyridine | 8 | 3 | — | — | 3 | 4 | 4 | — |
|  | 4 | 0 | 0 | 1 | 4 | 3 | 4 | — |
|  | 2 | 0 | 0 | 0 | 3 | 2 | 2 | — |
| 1-Allyloxy-6-chloro-2-(trifluoromethyl)-1H-imidazo(4,5-b)pyridine | 8 | 3 | — | — | 4 | 4 | 4 | — |
|  | 4 | 1 | 0 | 0 | 4 | 3 | 4 | — |
|  | 2 | 0 | 0 | 0 | 3 | 1 | 3 | — |
| 1-Isopropoxy-6-chloro-2-(trifluoromethyl)-1H-imidazo(4,5-b)pyridine | 8 | 2 | — | — | 4 | 4 | 4 | — |
|  | 4 | 1 | 0 | 1 | 4 | 2 | 4 | — |
|  | 2 | 0 | 0 | 0 | 2 | 1 | 3 | — |
| 1-(Allylcarbamoyloxy-6-chloro-2-(trifluoromethyl)-1H-imidazo-(4,5-b)pyridine | 8 | 2 | — | — | 3 | 3 | 4 | — |
|  | 4 | 0 | 1 | 1 | 3 | 3 | 2 | — |
|  | 2 | 1 | 2 | 1 | 2 | 0 | 2 | — |
| 1-Octanoyloxy-6-chloro-2-(trifluoromethyl)-1H-imidazo(4,5-b)pyridine | 8 | 2 | — | — | 3 | 4 | 4 | — |
|  | 4 | 1 | 4 | 1 | 4 | 2 | 4 | — |
| 1-(Methylcarbamoyloxy)- | 8 | 1 | — | — | 3 | 3 | 4 | — |

TABLE I-continued

| Compound | Lbs./Acre | Corn | Cotton | Soybean | Crabgrass | Pigweed | Foxtail | Velvet-leaf |
|---|---|---|---|---|---|---|---|---|
| 6-chloro-2-(trifluoromethyl)-1H-imidazo-(4,5-b)pyridine | 4 | 1 | 2 | 1 | 3 | 3 | 4 | — |
|  | 2 | 0 | 1 | 1 | 1 | 3 | 4 | — |
| 1-Methoxy-5-chloro-2-(trifluoromethyl)-1H-imidazo(4,5-b)pyridine | 8 | 3 | — | — | 4 | 4 | 4 | 4 |
|  | 4 | 2 | 0 | 2 | 3 | 3 | 4 | 4 |
|  | 2 | 0 | 0.5 | — | 3 | 3.5 | 3.5 | 4 |

NOTE:
Dashes indicate species which were not tested.

EXAMPLES 71–76

Representative compounds of the present invention were evaluated for postemergent application to plants including corn and several weed species. The evaluation was carried out in accordance with the procedures of Examples 62–70 except that the test solutions were applied about 9–12 days after the preparation and seeding of the flats. The results are as set forth in the following table:

out in the same manner as described in preceding examples.

Rating of the herbicidal effect was on a scale of 0–10, with 0 indicating no herbicidal effect, and 10 indicating non-emergence or death. In addition, the kind of herbicidal effect was observed and recorded in accordance with the following notation system:

A = Abscission of leaves
B = Burned
C = Chlorosis

TABLE II

| Compound | Lbs./Acre | Corn | Crab-grass | Pig-weed | Fox-tail | Velvet-leaf |
|---|---|---|---|---|---|---|
| 1-Acetoxy-6-chloro-2-(trifluoromethyl)-1H-imidazo-(4,5-b)pyridine | 8 | 4 | 4 | 4 | 4 | 4 |
|  | 4 | 4 | 4 | 4 | 4 | 4 |
|  | 2 | 4 | 4 | 4 | 4 | 4 |
|  | 1 | 2 | 4 | 4 | 4 | 4 |
| 1-Ethoxy-6-chloro-2-(trifluoromethyl)-1H-imidazo-(4,5-b)pyridine | 3 | 4 | 4 | 4 | 4 | 4 |
|  | 4 | 4 | 4 | 4 | 4 | 4 |
|  | 2 | 2 | 4 | 4 | 4 | 4 |
|  | 1 | 1 | 4 | 4 | 3 | 4 |
| 1-(3,6-Dichloro-2-methoxybenzoyloxy)-6-chloro-2-(trifluoromethyl)-1H-imidazo-(4,5-b)pyridine | 8 | 1 | 4 | 4 | 3 | 3 |
|  | 4 | 0 | 3 | 2 | 3 | 3 |
| 1-(Methylcarbamoyloxy)-6-chloro-2-(trifluoromethyl)-1H-imidazo(4,5-b)pyridine | 8 | 2 | 4 | 4 | 4 | 4 |
|  | 4 | 2 | 4 | 4 | 4 | 3 |
|  | 2 | 2 | 4 | 4 | 3 | 4 |
|  | 1 | 1 | 3.5 | 4 | 4 | 2.5 |
|  | ½ | 0 | 4 | 3 | 4 | 2 |
|  | ¼ | 0 | 4 | 3 | 3 | 2 |
| 1-Methoxy-6-amino-5,7-dibromo-2-(trifluoromethyl)-1H-imidazo-(4,5-b)-pyridine | 8 | 0 | 3 | 4 | 3 | 2 |
| 1-(Methylcarbamoyloxy)-6-chloro-5,7-dibromo-2-(trifluoromethyl)-1H-imidazo-(4,5-b)pyridine | 8 | 3 | 4 | 4 | 4 | 4 |

Essentially the same results as those reported in foregoing Examples 62–76 are obtained when evaluating the other representative compounds of Examples 1–61 hereinabove.

EXAMPLES 77–87

Other studies were carried out, evaluating various compounds of the present invention for preemergent application. These studies were made with a greater variety of plant species, at lower rates of application. Formulation of the compounds, however, was carried D = Death
E = Epinasty
F = Formative effects other than epinasty
G = Dark Green
I = Increased plant growth
L = Local necrosis
N = No germination
P = Purple pigmentation
R = Reduced germination
S = Stunting
U = Unclassified injury

TABLE III

| Compound | Lbs./Acre | Corn | Cotton | Soybean | Rice | Peanut | Corn | Soybean | Morning-glory | Cocklebur | Velvet-leaf | Foxtail Millet | Ragweed | Barnyard Grass |
|---|---|---|---|---|---|---|---|---|---|---|---|---|---|---|
| 1-Methoxy-6-chloro-2-(trifluoromethyl)-1H-imidazo(4,5-b)pyridine | 0.5 | 2SC | 0 | 0 | 0 | 0 | 0 | 0 | 10D | 4BC | 3BC | 5BC | 8BC | 8BC |
|  | 1.0 | 4SC | 3B | 5BC | 4BC | 0 | 2SC | 3CB | 10D | 10D | 7BC | 9BC | 10D | 9BC |
|  | 2.0 | 5SC | 7BC | 9BC | 6BC | 3C | 4SC | 8CB | 10D | 10D | 10D | 10D | 10D | 9.5BC |
| 1-Acetoxy-6-chloro-2- | 0.5 | 0 | 0 | 0 | 0 | 0 | 0 | 0 | 10D | — | 4BC | 4BC | 8BC | 2BC |

TABLE III-continued

| Compound | Lbs./Acre | Corn | Cotton | Soybean | Rice | Peanut | Corn | Soybean | Morning-glory | Cocklebur | Velvetleaf | Foxtail Millet | Ragweed | Barnyard Grass |
|---|---|---|---|---|---|---|---|---|---|---|---|---|---|---|
| (trifluoromethyl)-1H-imidazo(4,5-b)pyridine | 1.0 | 4SC | 6BC | 5BC | 4BC | 0 | 3SC | 6BC | 10D | 10D | 8BC | 5BC | 10D | 4BC |
|  | 2.0 | 5SC | 10D | 10D | 7BC | 3C | 6SC | 9BC | 10D | 10D | 9BC | 9.5BC | 10D | 8.5BC |
| 1-Ethoxy-6-chloro-2-(trifluoromethyl)-1H-imidazo(4,5-b)pyridine | 0.5 | 0 | 0 | 0 | 0 | 0 | 0 | 0 | 2BC | 0 | 0 | 0 | 8BC | 0 |
|  | 1.0 | 0 | 0 | 0 | 0 | 0 | 0 | 0 | 10D | 0 | 7BC | 8BC | 10D | 8BC |
|  | 2.0 | 2SC | 0 | 6BC | 5BC | 0 | 3SC | 9BC | 10D | 10D | 9BC | 10D | 10D | 9BC |
| 1-Benzyloxy-6-chloro-2-(trifluoromethyl)-1H-imidazo(4,5-b)pyridine | 0.5 | 0 | 0 | 0 | 0 | 0 | 0 | 0 | 0 | 0 | 0 | 0 | 4BC | 0 |
|  | 1.0 | 0 | 0 | 0 | 0 | 0 | 0 | 0 | 2SC | — | — | 5SC | 3BC | 4BC |
|  | 2.0 | 0 | 0 | 0 | 0 | 0 | 0 | 0 | 5BC | 0 | 3SC | 3SB | 3BC | 4BC |
| 1-Allyloxy-6-chloro-2-(trifluoromethyl)-1H-imidazo(4,5-b)pyridine | 0.5 | 0 | 0 | 0 | 0 | 0 | 0 | 0 | 9BC | 0 | 4BC | 0 | 6BC | 3BC |
|  | 1.0 | 0 | 0 | 0 | 0 | 0 | 0 | 0 | 10D | 0 | 8BC | 7BC | 9BC | 8BC |
|  | 2.0 | 0 | 0 | 0 | 3BC | 0 | 0 | 4BC | 10D | 5BC | 8.5BC | 9.5BC | 9BC | 9BC |
| 1-Isopropoxy-6-chloro-2-(trifluoromethyl)-1H-imidazo(4,5-b)pyridine | 0.5 | 0 | 0 | 0 | 0 | 0 | 0 | 0 | 8BC | 2C | 2BC | 0 | 6BC | 0 |
|  | 1.0 | 0 | 0 | 0 | 0 | 0 | 0 | 0 | 10D | 2C | 2BC | 2S | 9BC | 4BC |
|  | 2.0 | 2SC | 0 | 0 | 0 | 0 | 0 | 0 | 10D | — | 6BC | 8.5BC | 9.5BC | 9BC |
| 1-(Allylcarbamoyloxy-6-chloro-2-(trifluoromethyl)-1H-imidazo-(4,5-b)pyridine | 0.5 | 0 | 0 | 0 | 0 | 0 | 0 | 0 | 8BC | 4BC | 0 | 2S | 6BC | 0 |
|  | 1.0 | 0 | 0 | 0 | 2BC | 0 | 0 | 0 | 10D | 10D | 2BC | 4BC | 8BC | 6BC |
|  | 2.0 | 0 | 5BC | 5BC | 6BC | 2C | 2SC | 5BC | 10D | 10D | 5BC | 8BC | 10D | 8BC |
| 1-Octanoyloxy-6-chloro-2-(trifluoromethyl)-1H-imidazo(4,5-b)pyridine | 0.5 | 0 | 0 | 0 | 0 | 0 | 0 | 0 | 7BC | — | 0 | 0 | 5BC | 0 |
|  | 1.0 | 0 | 3C | 5BC | 3SB | 0 | 0 | 2C | 10D | — | 4BC | 4BS | 9BC | 6BC |
|  | 2.0 | 3SC | 7BC | 7BC | 5BC | 0 | 4SC | 7BC | 10D | 10D | 9BC | 8BC | 9.5BC | 7BC |
| 1-(2-Methoxy-3,6-dichlorobenzoyloxy)-6-chloro-2-(trifluoromethyl)-1H-imidazo(4,5-b)pyridine | 0.5 | 0 | 3F | 7F | 6F | 6F | 0 | 8F | 7F | 10D | 2F | 2S | 8F | 5FS |
|  | 1.0 | 2S | 5F | 10D | 8F | 10D | 0 | 10D | 8F | — | 8F | 3SF | 10D | 4FS |
|  | 2.0 | 4S | 9F | 10D | 9F | 9F | 1S | 10D | 10D | 10D | 10D | 4SF | 10D | 5FS |
| 1-(Methylcarbamoyloxy)-6-chloro-2-(trifluoromethyl)-1H-imidazo-(4,5-b)pyridine | 0.5 | 0 | 0 | 0 | 0 | 0 | 0 | 0 | 10D | — | 4BC | 2BC | 9BC | 5BC |
|  | 1.0 | 2SC | 3SC | 4BC | 4BC | 0 | 1SC | 3BC | 10D | 10D | 7BC | 8BC | 10D | 4BC |
|  | 2.0 | 4SC | 8BC | 10D | 6BC | 0 | 5SC | 10D | 10D | 10D | 10D | 10D | 10D | 10D |
| 1-Ethoxy-2,6-bis(trifluoromethyl)-1H-imidazo(4,5-b)pyridine | 0.5 | 0 | 0 | 0 | 0 | 0 | 0 | 0 | 7BC | — | 0 | 0 | 0 | 0 |
|  | 1.0 | 0 | 0 | 0 | 0 | 0 | 0 | 0 | 10D | — | 2BC | 0 | 7BC | 2S |
|  | 2.0 | 3SC | 2SC | 4BC | 2BC | 0 | 5SC | 8BC | 10D | 10D | 4BC | 9BC | 9BC | 3S |
| Control |  | 0 | 0 | 0 | 0 | 0 | 0 | 0 | 0 | 0 | 0 | 0 | 0 | 0 |
| Control |  | 0 | 0 | 0 | 0 | 0 | 0 | 0 | 0 | 0 | 0 | 0 | 0 | 0 |

EXAMPLE 88

1-Methoxy-6-chloro-2-(trifluoromethyl)-1H-imidazo-(4,5-b)pyridine was evaluated under field conditions. The compound was formulated in conventional procedures and applied as a soil surface spray to beds seeded with corn and selected weed species. The evaluations were carried out in a sub-tropical climate; there having been no rainfall in the first seven days following application, ½ inch of sprinkler irrigation was applied. Observations were made periodically for emergence, corn injury, and weed control. The results were as expressed in the following table, with date of observation expressed as the number of days from the day of seeding and compound application.

TABLE IV

| Compound | Rate (Lbs./Acre) | Emergence[a] | | | Crop Injury[c] | | | Percent weed Control—All Observations Day 17 | | | | | | |
|---|---|---|---|---|---|---|---|---|---|---|---|---|---|---|
|  |  | Day 5 | Day 7 | Day 11 | Day 11 | Day 17 | Day 38 | Prickly sida | Venice mallow | Common purslane | Morning glory | Foxtail millet | Black nightshade | Pigweed |
| 1-methoxy-6-chloro-2-(trifluoromethyl)-1H-imidazo(4,5-b)pyridine | 1 | 97 | 90 | 89 | 0.0 | 0.0 | 0.0 | 98 | 90 | 100 | 89 | 98 | 100 | 100 |
|  | 1.5 | 97 | 89 | 87 | 0.0 | 0.3 | 0.0 | 99 | 97 | 100 | 100 | 99 | 100 | 100 |
|  | 2 | 72 | 94 | 95 | 0.0 | 0.7 | 0.0 | 99 | 96 | 100 | 91 | 99 | 100 | 100 |
|  | 3 | 100+ | 100 | 98 | 0.3 | 2.3 | 1.7 | 100 | 100 | 100 | 96 | 100 | 100 | 100 |
|  | 4 | 96 | 85 | 83 | 2.0 | 3.7 | 4.3 | 100 | 100 | 100 | 100 | 100 | 100 | 100 |
| Control | 0 | 100 (72)[b] | 100 (108) | 100 (109) | 0.0 | 0.0 | 0.0 | 0 (14.6)[d] | 0 (5.6) | 0 (3.8) | 0 (5) | 0 (24.5) | 0 (2.6) | 0 (4.1) |

[a]Emergence expressed as a percent of the control.
[b]Number of emerged corn seedings per 15 feet of row.
[c]Crop injury on a 0-10 scale where 0 = no injury, 1-3 = slight, 4-6 = moderate, 7-9 = severe, and 10 = death of all plants.
[d]Weeds/sq.ft. based on 5 one sq. ft. counts per plot.

as noted above, the compounds of the present invention can be used in conjunction with other agricultural materials, including other herbicides. Thus, in one embodiment, the present invention is directed to a method which comprises applying essentially simultaneously to a plant part an amount of a first substance which is:

1-methoxy-6-chloro-2-trifluoromethyl-1H-imidazo(4,5-b)-pyridine, 1-methoxy-5-chloro-2-trifluoromethyl-1H-imidazo(4,5-b)-pyridine, or 1-methoxy-2,6-bis(trifluoromethyl)-1H-imidazo(4,5-b)-pyridine;

and an amount of a second substance which is:
alachlor,
atrazine,
butylate,
2-chloro-4-(1-cyano-1-methylethylamino)-6-ethylamino-s-triazine,
dalapon,
dinoseb,
diuron,
EPTC,
linuron,
oryzalin,
propachlor,
propazine,
simazine,
trifluralin, or
TCA,
the amounts being such as to effect, in combination, growth inhibition. This embodiment of the present invention also comprehends a combination of the first and second substances, which combination is useful in implementing the method.

The substances serving as the second substance of the present herbicidal methods and combinations are in every instance known compounds. For a convenient compilation of information and references on these and other known herbicides, attention is directed to the *Herbicide Handbook of the Weed Society of America*, sec. ed., published by The W. F. Humphrey Press, Inc., Geneva, New York, 1970, and available from Weed Science Society of America, Department of Agronomy, University of Illinois, Urbana, Illinois 61801.

The known herbicides serving as the second substance are generally crystalline solids, typically white in color; the exceptions are butylate (an amber liquid); EPTC (a light yellow-colored liquid); and dinoseb (which may exist as either a dark brown solid or a dark orange liquid, depending on temperature). Each of these compounds is individually effective at a range of rates, depending upon the particular substance, the particular use (for example, whether a selective or general herbicidal effect is sought), and the type of soil and other growing conditions. The generally established rate ranges for these known herbicides, when used individually, are as follows:

| Compound | Established Rate in Lbs./Acre |
|---|---|
| alachlor | 1–4 |
| atrazine | 2–4 |
| butylate | 3–4 |
| 2-chloro-4-(1-cyano-1-methylethylamino)-6-ethylamino-s-triazine | 1–4 |
| dalapon | .75–20 |
| dinoseb | .75–12 |
| diuron | 0.6–6.4 (selective) |
| | 4–16 (general) |
| EPTC | 2–6 |
| linuron | 0.5–3 (selective) |
| | 1–3 (non crop) |
| oryzalin | 1–4 |
| propachlor | 3–6 |
| propazine | 1–4 |
| simazine | 2–4 |
| trifluralin | 0.5–2 |
| TCA | 4—30 (selective) |
| | 50–200 (general) |

(Herbicide Handbook of the Weed Society of America, supra).

In employing these known herbicides in combination with the herbicides of the present invention, the precise ratio of the herbicidal agents to one another is not critical. It is generally preferred that the known herbicide be used in an amount within its established rate range for individual use as sole herbicidal agent, although because of the herbicidal effect attributable to the ether, lesser amounts within the established rate range or amounts below the established rate range are appropriate. Thus, amounts below the median of the established rate range generally give good results in combination with the specified ethers. However, each of the ether and known herbicide components should be employed in an amount which, if employed individually as sole herbicidal agent, would exert at least a minimal plant-growth inhibiting effect. In the case of alachlor, atrazine, and propachlor, for example, the established rate ranges are 1–4 lbs./acre of alachlor, 2–4 lbs./acre of atrazine, or 3–6 lbs./acre of propachlor; but good results generally are obtained in the present combinations at application rates of 2.5 lbs./acre or less of alachlor, 3 lbs./acre or less of atrazine, or 4.5 lbs./acre or less of propachlor. For the specified ethers serving as the first component, application rates of 0.25–4 lbs./acre are desirable for selective activity, and preferred rates for selective activity are generally 1–2.5 lbs./acre.

The substances can be administered separately, although preferably essentially simultaneously, and this mode of administration is sometimes preferred. Thus, for example, different herbicides may require different modes of applications which preclude a single application. In particular, each of butylate and EPTC is preferably applied to corn prior to planting and with mechanical mixing into the soil. The ethers of the present invention are preferably applied to corn immediately after seeding but without mechanical mixing. Thus, separate administration is sometimes preferred in order to make best utilization of the respective herbicidal properties. Where separate administration is preferred, the exact interval between applications is not critical; but optimal results generally are obtained when the respective administrations are essentially simultaneously, such as within several minutes to not more than within several hours of one another. The time interval between applications is largely dictated by the practicalities of agricultural practices.

Generally, however, it is preferred that both substances be formulated as a single formulation. The formulation is conducted in accordance with conventional procedures, utilizing such adjuvants as surface-active agents, inert finely-divided solids, and the like. Reference is made to the discussion hereinabove concerning formulation of the compounds of the present invention, generally. Where the objective is selective herbicidal activity, it is generally preferred that the specified ether comprise at least 40 percent by weight of the total herbicidally-active component.

EXAMPLES 89–103

1-Methoxy-6-chloro-2-trifluoromethyl-1H-imidazo(4,5-b)pyridine was evaluated in combination with each of a number of known herbicides. The evaluation was conducted in each case in accordance with the standard screening procedures described in preceding examples, each of the herbicides being applied separately but within rapid succession (within an interval of not longer than about 5 minutes).

The results observed were as set forth in the following tables.

TABLE V

COMBINATION OF 1-METHOXY-6-CHLORO-2-TRIFLUOROMETHYL-1H-IMIDAZO(4,5-b)PYRIDINE ("A") WITH ALACHLOR ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A+B | 0.25+0.5 | 10D | 0 | 10D | 9SB | 10N | 9.5RS | 9.5RS | 3SB | 9SR | 4SB | 0 | 6SB | 9SB | 9S |
| " | 0.25+1 | 10D | 0 | 10D | 9SR | 10N | 9.9SR | 10N | 5SB | 10N | 7SB | 0 | 10D | 10D | 10N |
| " | 0.25+2 | 10D | 1S | 10D | 9.5RS | 10N | 10N | 10N | 9SF | 10N | 9SB | 0 | 9BS | 10D | 10N |
| " | 0.25+4 | 10D | 2S | 10N | 10D | 10N | 10N | 10N | 8SF | 10N | 9BS | 2S | 9BS | 10D | 10N |
| " | 0.5+0.5 | 10D | 0 | 10D | 10D | 10N | 9.5RS | 9.5RS | 3SB | 8S | 8SB | 1S | 8BS | 9BS | 10N |
| " | 0.5+1 | 10D | 0 | 10N | 10D | 10N | 10D | 9.5RS | 4BSF | 8RS | 8BSR | 0 | 9.5BS | 10N | |
| " | 0.5+2 | 10D | 3S | 10D | 9.5BSR | 10N | 10N | 10N | 10D | 8SF | 10N | 9BS | 0 | 9BS | 9.5BS | 9RS |
| " | 0.5+4 | 10D | 3S | 10N | 10N | 10N | 10N | 10N | 9FSR | 9.8RS | 9.5BS | 2S | 9.5BS | 10N | 10N |
| " | 1+0.5 | 10D | 2SB | 10D | 10D | 10N | 9.5BS | 9.5RS | 7BS | 8BSR | 9BS | 0 | 9BS | 7BS | 9RS |
| " | 1+1 | 10D | 1S | 10D | 10D | 10N | 9.8RS | 9.8RS | 8BS | 9RS | 10D | 3S | 9BS | 10D | 10N |
| " | 1+2 | 10D | 3S | 10N | 9.8RSB | 10N | 9.8RS | 10N | 8BSF | 9.5RS | 10D | 0 | 9.5BS | 10D | 10N |
| " | 1+4 | 10D | 3S | 10D | 9.5BSR | 10N | 10D | 10N | 9BSF | 9.5RS | 9SB | 2S | 9.5BS | 10D | 10N |
| " | 2+0.5 | 10D | 3S | 10D | 8S | 10N | 9.8RS | 9.5RS | 9.5BS | 7SB | 10D | 3S | 9.5BS | 9BS | 9.8RS |
| " | 2+1 | 10D | 1S | 10D | 9.5RS | 10N | 10N | 9.8RS | 9 | 9RS | 8BS | 1S | 9.8BS | 9BS | 10N |
| A+B | 2+2 | 10D | 0 | 10D | 9.8RS | 10N | 10N | 10N | 9BS | 10D | 9.5BS | 1SB | 9.5BS | 10D | 10N |
| " | 2+4 | 10D | 3S | 10D | 10D | 10N | 10N | 10N | 9.5BSF | 10N | 9.5BS | 4SB | 9.8BS | 10D | 10N |
| Control | 0 | 0 | 0 | 0 | 0 | 0 | 0 | 0 | 0 | 0 | 0 | 0 | 0 | 0 | 0 |

TABLE VI:

COMBINATION F 1-METHOXY-6-CHLORO-2-TRIFLUOROMETHYL-1H-IMIDAZO(4,5-b)PYRIDINE ("A") WITH ATRAZINE ("B")

| Compounds | Rates Lbs./Acre | Morning Glory | Pigweed | Ragweed | Corn | Velvet Leaf | Lambs Quarter | Jimson Weed | Barnyard Grass | Rice | Large Crabgrass | Corn | Foxtail millet | Sorghum | Johnson Grass |
|---|---|---|---|---|---|---|---|---|---|---|---|---|---|---|---|
| A+B | ¼ ¼ | 8SD | 9RS | 8RS | 0 | 3BS | 7RS | 8.5SD | 5BS | 2BS | 4S | 0 | 3S | 0 | 2S |
| " | ¼ ½ | 10D | 9.5RS | 8RDS | 0 | 5BS | 7RSD | 9SD | 8SD | 3BS | 4S | 0 | 4BS | 0 | 2S |
| " | ¼ 1 | 9.5SD | 10N | 8RDS | 0 | 7SD | 7RS | 9SD | 9.5SD | 3BS | 6S | 0 | 4BS | 0 | 4BS |
| " | ¼ 2 | 10D | 9.5RS | 9.5RDS | 0 | 9.5SD | 7RS | 9.5SD | 9.5SD | 3BS | 8S | 0 | 7SD | 0 | 4BS |
| " | ½ ¼ | 10D | 9.5RS | 6.5SD | 0 | 7SD | 7.5RS | 9SD | 9SD | 3BS | 7RS | 0 | 8SD | 0 | 4BS |
| " | ½ ½ | 10D | 9RS | 9SD | 0 | 7SD | 5RS | 9.5SD | 9SD | 4BS | 7RS | 0 | 7SD | 0 | 7SD |
| " | ½ 1 | 10D | 9.5RS | 9.5RSD | 1S | 6SD | 6.5RS | 9SD | 9SD | 3BS | 8SD | 0 | 8.5SD | 0 | 6.5SD |
| " | ½ 2 | 10D | 9RS | 9.5RSD | 0 | 9SD | 7RS | 8.5SD | 10D | 3BS | 9SD | 0 | 9.5SD | 0 | 6.5SD |
| " | 1 ¼ | 10D | 9RS | 9SD | 0 | 6.5SD | 7RS | 9SD | 9.5SD | 3BS | 9.5SD | 0 | 10D | 3BS | 7SD |
| " | 1 ½ | 10D | 9.5RS | 9.5SD | 0 | 9SD | 7RS | 9.5SD | 9.5SD | 2BS | 9.5SD | 0 | 10D | 4BS | 8SD |
| " | 1 1 | 10D | 9.5RS | 10D | 0 | 9SD | 8RS | 9.5SD | 10D | 3BS | 9.5SD | 0 | 10D | 4BS | 7SD |
| " | 1 2 | 10D | 9.5RS | 10D | 0 | 9SD | 7RSD | 9.5SD | 10D | 3BS | 9.5SD | 0 | 10D | 3BS | 9SD |
| " | 2 ¼ | 10D | 9.5RS | 9SD | 1S | 9.5SD | 7RS | 9.5SD | 10D | 3BS | 9.5SD | 0 | 10D | 7SD | 9.5SD |
| " | 2 ½ | 10D | 9.5RS | 10D | 0 | 9.5SD | 7.5RS | 9.5SD | 10D | 4BS | 10D | 0 | 10D | 8SD | 9SD |
| " | 2 1 | 10D | 9.5RS | 10D | 2S | 10D | 8RS | 9.5SD | 9.5SD | 5BS | 9.5SD | 1S | 10D | 8SD | 9SD |
| " | 2 2 | 10D | 9.5RS | 10D | 2S | 10D | 8RS | 10D | 10D | 4BS | 9.5SD | 0 | 10D | 7SD | 9SD |
| Control | — — | 0 | 0 | 0 | 0 | 0 | 0 | 0 | 0 | 0 | 0 | 0 | 0 | 0 | 0 |
| Control | — — | 0 | 0 | 0 | 0 | 0 | 0 | 0 | 0 | 0 | 0 | 0 | 0 | 0 | 0 |
| Control | — — | 0 | 0 | 0 | 0 | 0 | 0 | 0 | 0 | 0 | 0 | 0 | 0 | 0 | 0 |

TABLE VII

COMBINATION OF 1-METHOXY-6-CHLORO-2-TRIFLUOROMETHYL-1H-IMIDAZO(4,5-b)PYRIDINE ("A") WITH BUTYLATE ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A+B | 0.25 + 1.0 | 10D | 0 | 7SF | 5SB | 3S | 4SB | 9.5BS | 9SF | 0 | 10D | 0 | 4SB | 9SR | 10D |
| " | 0.25 + 2.0 | 6SB | 0 | 9SF | 6SB | 8S | 6SB | 9BS | 10D | 3S | 10D | 0 | 6SB | 9.5RS | 10D |
| " | 0.25 + 3.0 | 10D | 0 | 9SBF | 4SB | 8SB | 10D | 9BSR | 10D | 7S | 10D | 0 | 7SB | 10D | 10D |
| " | 0.25 + 4.0 | 10D | 0 | 9SB | 8SB | 8SB | 10D | 10D | 10D | 9SB | 10D | 0 | 7SB | 10D | 10D |
| 41 | 0.5 + 1.0 | 10D | 1S | 6SB BS | 9.5 | 7SB | 5SB | 8BS SBF | 3S | 10D | 2S | 9BS | 9RSB | 10D | |
| " | 0.5 + 2.0 | 9BS | 1S | 8BS | 10D | 8SB | 9.5RS | 10D | 10D | 6S | 10D | 1S | 8BS | 9RS | 10D |
| " | 0.5 + 3.0 | 10D | 3S | 9.5BS | 9.5 RS | 10D | 10D | 10D | 10D | 9.5S | 10D | 1S | 9BS | 10D | 10D |
| " | 0.5 + 4.0 | 10D | 4S | 9.5 BSR | 9.5 BSR | 10D | 10D | 10D | 10D | 9.5S | 10D | 3S | 9BS | 10D | 10D |
| " | 1.0 + 1.0 | 10D | 5S 10D | 10D | 9.5BS | 9BS | 9.5 BS | 9.5 BS | 3B | 10D | 4S | 9BS | 9BS | 10D | |
| " | 1.0 + 2.0 | 10D | 5S | 10D | 10D | 9.5BS | 10D | 10D | 10D | 8S | 10D | 4S | 9BS | 10D | 10D |
| " | 1.0 + 3.0 | 10D | 4S | 10D | 10D | 8BS | 9BS | 10D | 10D | 5S | 10D | 3S | 7BS | 9.5BS | 10D |
| " | 1.0 + 4.0 | 10D | 3S | 10D | 10d | 9.5 BSR | 9.5BS | 9.5 FS | 9SF | 7S | 10D | 3S | 9BS | 10D | 10D |
| " | 2.0 + 1.0 | 10D | 5S | 10D | 10D | 9.5BS | 9BS | 9BS | 8 BSF | 3B | 10D | 5SB | 8SB | 9BS | 10D |
| " | 2.0 + 2.0 | 10D | 5S | 10D | 10D | 9.5BS | 10D | 8S | 9.5 | 5S BSF | 10D | 6SB | 8BS | 9BSR | 9SB |
| A+B | 2.0 + 3.0 | 10D | 6SB | 10D | 10D | 10D | 9.5BS | 9.5 SB | 10D | 8S | 10D | 5S | 8BS | 9.5RS | 10D |
| " | 2.0 + 4.0 | 10D | 6SB | 10D | 10D | 10D | 9.5 BS | 9.5 | 10D | 9S | 10D | 6SB | 9BS | 10D | 10D |
| Control | 0 | 0 | 0 | 0 | 0 | 0 | 0 | 0 | 0 | 0 | 0 | 0 | 0 | 0 | 0 |

TABLE VIII

COMBINATION OF 1-METHOXY-6-CHLORO-2-TRIFLUOROMETHYL-1H-IMIDAZO(4,5-b) PYRIDINE ("A") WITH 2-CHLORO-4-(1-CYANO 1-METHYLETHYLAMINO)-6-ETHYLAMINO-s-TRIAZINE ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.25 | 10D | 0 | 10D | 10D | 4SB | 6SB | 5S | 3SB | 4S | 9BS | 2S | 9BS | 7BS | 8SB |
| " | 0.25 + 0.5 | 10D | 3S | 10D | 10D. 7SB | 9.5BS | 7S | 8BS | 9BS | 9.5 | 2S BS | 9.5BS | 9.5BS | 8SB | |
| " | 0.25 + 1.0 | 10D | 4S | 10D | 10D | 9.5BS | 10D | 7SB | 6SB | 8BS | 10D | 3S | 10D | 10D | 9.5BS |
| " | 0.25 + 2.0 | 10D | 5S | 10D | 10D | 10D | 10D | 10D | 9.5 BS | 10D | 10D | 4SB | 9.5BS | 9.5BS | 9.5BS |
| " | 0.5 + 0.25 | 10D | 3S | 10D | 10D | 8SB | 7SB | 6SB | 6SB | 8B | 9BS | 3S | 9BS | 9.5BS | 8S |
| " | 0.5 + 0.5 | 10D | 2S | 10D | 10D | 8SB | 9.5SB | 6SB | 6SB | 8B | 10D | 2S | 9BS | 9.5BS | 9SB |
| " | 0.5 + 1.0 | 10D | 2SB | 10D | 10D | 9.5SB | 10D | 9.5 BS | 9.5 BS | 10D | 9.8 BS | 2SB | 9.5BS | 9BS | 9SB |
| " | 0.5 + 2.0 | 10D | 3SB | 10D | 10D | 9.5BS | 10D | 9.5 BS | 9.8 BS | 10D | 10D | 2S | 9.5BS | 10D | 9.58SB |
| " | 1.0 + 0.25 | 9.5BS | 2S | 10D | 10D | 9.5BS | 10D | 8SB | 7SB | 7B | 9.5BS | 2S | 9.5BS | 9.5BS | 9SB |
| " | 1.0 + 0.5 | 10D | 2SB | 10D | 10D | 9.5BS | 10D | 9.5 BS | 9.5 BS | 10D | 10D | 2S | 9.5SB | 10D | 9S |
| " | 1.0 + 1.0 | 10D | 2SB | 10D | 10D | 9.5BS | 9.8BS | 9.5 SB | 9.5 BS | 10D | 10D | 2S | 10D | 9.5BS | 9.5SB |
| " | 1.0 + 2.0 | 10D | 4SB | 10D | 10D | 9.5BS | 10D | 9.5 BS | 10D | 10D | 9.8 BS | 3S | 9.5BS. 10D | 9SB | |
| " | 2.0 + 0.25 | 10D | 2S | 10D | 10D | 9.5BS | 9.5BS | 9.5 BS | 8SB SB | 7BS | 9.5 BS | 3S | 9.5BS | 9.5BS | 9SB |
| " | 2.0 + 0.5 | 10D | 5SB | 10D | 10D | 10D | 10D | 9.5 BS | 9.5 BS | 10D | 10D | 5SB | 9.5BS | 10D | 10D |
| " | 2.0 + 1.0 | 10D | 4SB | 10D | 10D | 10D | 10D | 9.8 BS | 10D | 10D | 10D | 3SB | 10D | 10D | 9SB |
| " | 2.0 + 2.0 | 10D | 4SB | 10D | 10D | 10D | 10D | 9.5 BS | 10D | 10D | 10D | 5SB | 10D | 10D | 10D |
| Control | 0 | 0 | 0 | 0 | 0 | 0 | 0 | 0 | 0 | 0 | 0 | 0 | 0 | 0 | 0 |

TABLE IX:

COMBINATION OF 1-METHOXY-6-CHLORO-2-TRIFLUOROMETHYL-1H-IMIDAZO(4,5-b)PYRIDINE ("A") WITH DALAPON ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.75 | 3SBC | 0 | 4SB | 3S | 0 | 2S | 4S | 0 | 0 | 3SB | 0 | 0 | 0 | 0 |
| " | 0.25 + 1.5 | 2B | 0 | 6BS | 10D | 0 | 0 | 4B | 0 | 2S | 3S | 0 | 0 | 0 | 0 |
| " | 0.25 + 3.0 | 2B | 0 | 9BS | 10D | 0 | 7SB | 3BS | 0 | 6SB | 4S | 0 | 4B | 0 | 3S |
| " | 0.25 + 6.0 | 3SB | 0 | 10D | 9BS | 3BS | 8BS | 4BS | 3BS | 5SB | 3SB | 0 | 4BS | 0 | — |
| " | 0.5 + 0.75 | 6SB | 0 | 8BSR | 10D | 2S | 5SB | 5SB | 0 | 0 | 4S | 0 | 7BS | 3S | 7SR |
| " | 0.5 + 1.5 | 9BS | 0 | 9BS | 10D | 4BS | 8BS | 3B | 1S | 3S | 6SB | 0 | 8BS | 0 | 6RS |
| " | 0.5 + 3.0 | 9BS | 1S | 10D | 10D | 5SB | 7SB | 3B | 1S | 5SB | 7SB | 0 | 6BS | 2S | 7RS |
| " | 0.5 + 6.0 | 10D | 0 | 10D | 9.5BS | 7BS | 8BS | 10D | 3SB | 7BS | 7SB | 0 | 8BS | 2S | 7RS |
| " | 1.0 + 0.75 | 9.5BS | 0 | 10D | 10D | 6BS | 10D | 6BS | 3SB | 5BS | 9.5BS | 0 | 10D | 4S | 6SR |
| " | 1.0 + 1.5 | 9.5BS | 0 | 10D | 10D | 4SB | 9BS | 7BS | 2SB | 4B | 10D | 0 | 10D | 3SB | 7SR |
| " | 1.0 + 3.0 | 10D | 0 | 10D | 10D | 5BS | 9.5BS | 9BS | 3SB | 5BS | 10D | 0 | 10D | 6BS | 7RS |
| " | 1.0 + 6.0 | 10D | 4F | 10D | 10D | 7BSR | 10D | 10D | 6BSF | 9BS | 10D | 4FS | 10D | 4SB | 8S |
| " | 2.0 + 0.75 | 10D | 0 | 10D | 10D | 4BS | 7BS | 9BS | 8BS | 6BS | 9.5BS | 2S | 10D | 8BS | 10D |
| " | 2.0 + 1.5 | 10D | 3S | 10D | 10D | 9BS | 10D | 9BS | 8BS | 9BS | 10D | 3S | 10D | 7BS | 10D |
| " | 2.0 + 3.0 | 10D | 1S | 10D | 10D | 9BS | 10D | 10D | 9BS | 9BS | 10D | 2S | 10D | 7BS | 9RS |
| " | 2.0 + 6.0 | 10D | 2S | 10D | 10D | 9.5BS | 10D | 10D | 6BS | 8BS | 10D | 4SB | 9.5BS | 8BS | 9RS |
| Control | 0 | 0 | 0 | 0 | 0 | 0 | 0 | 0 | 0 | 0 | 0 | 0 | 0 | 0 | 0 |

TABLE X:

COMBINATION OF 1-METHOXY-6-CHLORO-2-TRIFLUOROMETHYL-1H-IMIDAZO(4,5-b)PYRIDINE ("A") WITH DINOSEB ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quartert |
|---|---|---|---|---|---|---|---|---|---|---|---|---|---|---|---|
| A + B | 0.25 + 1.0 | 2B | 0 | 0 | 7SB | 0 | 2S | 2S | 0 | 0 | 3SB | 0 | 7SB | 2S | 5S |
| " | 0.25 + 2.0 | 5SB | 0 | 2S | 10D | 0 | 0 | 2S | 0 | 0 | 3SB | 0 | 8BS | 0 | 5S |
| " | 0.25 + 4.0 | 9BS | 0 | 2S | 10D | 2S | 2S | 6S | 0 | 0 | 3S | 0 | 9BS | 0 | 5S |
| " | 0.25 + 8.0 | 9BS | 0 | 4S | 10D | 4SR | 5RS | 8SR | 2S | 3S | 3S | 1S | 10D | 2S | 6S |
| " | 0.5 + 1.0 | 6SB | 0 | 3SB | 10D | 5SB | 8BS | 8SR | 2S | 3BS | 5SB | 0 | 9.5BS | 2S | 7S |
| " | 0.5 + 2.0 | 10D | 0 | 8BS | 10D | 4SB | 6SB | 9SB | 1SB | 1B | 5SB | 0 | 9.5BS | 3SB | 9SR |
| " | 0.5 + 4.0 | 10D | 0 | 7SB | 10D | 4SB | 8BSR | 7SR | 2SB | 2SB | 6SB | 0 | 9.5BS | 2SB | 7SR |
| " | 0.5 + 8.0 | 10D | 2S | 7SB | 10D | 7SR | 7SRB | 6SR | 3S | 2SB | 5SB | 0 | 10D | 2S | 9SR |
| " | 1.0 + 1.0 | 10D | 2S | 10D | 10D | 9SB | 9.5RS | 10N | 7BS | 10D | 10D | 1S | 9.5BS | 8BS | 10D |
| " | 1.0 + 2.0 | 10D | 1S | 10D | 10D | 9BS | 10D | 10D | 8BS | 4BS | 7BS | 1S | 10D | 6BS | 10D |
| " | 1.0 + 4.0 | 10D | 2SB | 10D | 10D | 8BS | 10D | 10D | 6BS | 4BS | 8BS | 0 | 10D | 7BS | 10D |
| " | 1.0 + 8.0 | 10D | 1S | 7BS | 10D | 7BS | 10D | 9.5RS | 4BS | 6BS | 10D | 0 | 10D | 6BS | 10D |
| " | 2.0 + 1.0 | 10D | 4SB | 10D | 10D | 10D | 10D | 9SB | 9BS | 8BS | 10D | 4SB | 10D | 10D | 10D |
| " | 2.0 + 2.0 | 10D | 3S | 10D | 10D | 10D | 10D | 10D | 10D | 8BS | 10D | 4SB | 10D | 9.5BS | 10D |
| A + B | 2.0 + 4.0 | 10D | 2S | 10D | 10D | 9.5BS | 10D | 10D | 9BS | 8BS | 10D | 1S | 10D | 9.5BS | 10D |
| " | 2.0 + 8.0 | 10D | 3SB | 10D | 10D | 10D | 10D | 10D | 8BS | 8BSC | 10D | 2S | 10D | 10D | 10D |

TABLE X:-continued
COMBINATION OF 1-METHOXY-6-CHLORO-2-TRIFLUOROMETHYL-1H-IMIDAZO(4,5-b)PYRIDINE ("A") WITH DINOSEB ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quartert |
|---|---|---|---|---|---|---|---|---|---|---|---|---|---|---|---|
| Control | 0 | 0 | 0 | 0 | 0 | 0 | 0 | 0 | 0 | 0 | 0 | 0 | 0 | 0 | 0 |

TABLE XI
COMBINATION OF 1-METHOXY-6-CHLORO-2-TRIFLUOROMETHYL-1H-IMIDAZO(4,5-b)PYRIDINE ("A") WITH DIURON ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.25 | 10D | 0 | 4SB | 10D | 4BS | 5SB | 8BS | 1B | 1B | 5BS | 0 | 7BS | 2SB | 8SR |
| " | 0.25 + 0.5 | 6BSL | 0 | 5BS | 10D | 9BS | 8BS | 9BS | 2B | 4B | 8BS | 0 | 9BS | 3BS | 9SR |
| " | 0.25 + 1.0 | 10D | 0 | 8BS | 10D | 10D | 9BS | 9BS | 3BC | 3B | 10D | 3S | 9BS | 8BS | 9SR |
| " | 0.25 + 2.0 | 10D | 5BS | 10D | 10D | 10D | 9.5BS | 9BS | 4BS | 7B | 10D | 5SB | 9BS | 9.5BS | 10N |
| " | 0.5 + 0.25 | 10D | 2B | 8BS | 10D | 7BS | 8BS | 9.5RS | 3SB | 4B | 9BS | 0 | 9BS | 7BS | 9RS |
| " | 0.5 + 0.5 | 9BS | 2SB | 10D | 9.5BS | 9BS | 8BS | 9BS | 2S | 4B | 9BS | 0 | 9BS | 9.5BS | 9.5RS |
| " | 0.5 + 1.0 | 10D | 2S | 10D | 10D | 10D | 9BS | 9.5BS | 2SB | 4B | 10D | 5SB | 9.5BS | 9.5BS | 9RS |
| " | 0.5 + 2.0 | 10D | 5SB | 10D | 10D | 10D | 9BS | 9BS | 3CSB | 5B | 10D | 4SB | 9BS | 9BS | 9RS |
| " | 1.0 + 0.25 | 10D | 2S | 10D | 10D | 10D | 9.5BS | 9.5BS | 3SB | 4B | 10D | 2S | 9.5BS | 9.5BS | 10N |
| " | 1.0 + 0.5 | 10D | 4SB | 10D | 10D | 10D | 9.5BS | 9.5BS | 7BS | 9B | 10D | 4SB | 10D | 10D | 9.5RS |
| " | 1.0 + 1.0 | 10D | 7SB | 10D | 10D | 10D | 9.5BS | 9.5BS | 10D | 9B | 10D | 8BS | 9BS | 10D | 9.5RS |
| " | 1.0 + 2.0 | 10D | 4SB | 10D | 10D | 10D | 9.5BS | 9.5BS | 10D | 9.5B | 10D | 7BS | 9.5BS | 10D | 9.5RS |
| " | 2.0 + 0.25 | 10D | 5SB | 10D | 10D | 10D | 9.5BS | 10D | 9BS | 9B | 10D | 4SB | 9.5BS | 10D | 10N |
| " | 2.0 + 0.5 | 10 | 7SB | 10D | 10D | 10D | 9.5BS | 9.5BS | 9.5B | 9B | 10D | 6SB | 9.5BS | 10D | 9.5RS |
| A + B | 2.0 + 1.0 | 10D | 7SB | 10D | 10D | 10D | 9.5BS | 10D | 10D | 9.5B | 10D | 6SB | 9.5BS | 10D | 10N |
| " | 2.0 + 2.0 | 10D | 7SB | 10D | 10D | 10D | 9.5BS | 10D | 9B | 9.5B | 10D | 8BS | 9.5BS | 10D | 10N |
| Control | 0 | 0 | 0 | 0 | 0 | 0 | 0 | 0 | 0 | 0 | 0 | 0 | 0 | 0 | 0 |

TABLE XII:
COMBINATION OF 1-METHOXY-6-CHLORO-2-TRIFLUOROMETHYL-1H-IMIDAZO(4,5-b)PYRIDINE ("A") WITH EPTC ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 1.0 | 10D | 3S | 9BS | 8SB | 7BS | 6BS | 8SB | 10D | 8S | 10D | 0 | 8BS | 10D | 9.5 RS |
| " | 0.25 + 2.0 | 10D | 2S | 9BS | 10D | 9BSF | 9.5RSB | 10N | 10D | 10N | 10D | 4S | 9BS | 10D | 10N |
| " | 0.25 + 3.0 | 10D | 7FS | 9.5BS | 10D | 9BSF | 10D | 10N | 10D | 9.8RS | 10D | 4S | 10D | 10N | 10N |
| " | 0.25 + 4.0 | 10D | 8FS | 10D | 10D | 9BSF | 10D | 10N | 10D | 10N | 10D | 7FS | 9BSR | 10N | 9.5RS |
| " | 0.5 + 1.0 | 10D | 1S | 10D | 10D | 8BS | 7BS | 10D | 10D | 8BSR | 10D | 4S | 9BS | 10D | 10N |
| " | 0.5 + 2.0 | 10D | 5SF | 10D | 10D | 9.5BSR | 10D | 10N | 9.8RSF | 9.5RS | 10D | 4S | 9BS | 10D | 10N |
| " | 0.5 + 3.0 | 10D | 7FS | 10D | 10D | 9.5BSF | 10D | 10N | 10D | 10N | 10D | 6SF | 9.5BS | 10D | 9.8RS |
| " | 0.5 + 4.0 | 10D | 8FS | 10D | 10D | 9.8BS | 10N | 10N | 10D | 10N | 10D | 8FS | 9BS | 10D | 10N |
| " | 1.0 + 1.0 | 10D | 4S | 10D | 10D | 9.8BS | 9.5BS | 9.5BSR | 10D | 8SB | 9.5BS | 4S | 9.5BS | 9.5BS | 9RS |
| " | 1.0 + 2.0 | 10D | 8SB | 10D | 10D | 10D | 10D | 10N | 10D | 10D | 10D | 5S | 9BS | 10D | 9.5RS |
| " | 1.0 + 3.0 | 10D | 7SBF | 10D | 10D | 10D | 10D | 10D | 10D | 10N | 10D | 8BSF | 9.5BS | 10D | 9.5RS |
| " | 1.0 + 4.0 | 10D | 7SB | 10D | 10D | 10D | 10D | 10N | 10D | 10D | 10D | 8SBF | 10D | 10D | 9.8RS |
| " | 2.0 + 1.0 | 10D | 7SB | 10D | 10D | 10D | 10D | 9.5RSB | 10D | 8SB | 10D | 7SB | 9BS | 10D | 9.5RS |
| " | 2.0 + 2.0 | 10D | 8SB | 10D | 9SB | 10D | 10D | 9.5RSB | 10D | 10D | 10D | 7SB | 10D | 10D | 10N |
| " | 2.0 + 3.0 | 10D | 10D | 10D | 10D | 10D | 10D | 10N | 10D | 10N | 9.8BSR | 9SB | 10D | 10D | 9.8RS |
| " | 2.0 + 4.0 | 10D | 10D | 10D | 10N | 10D | 10D | 10N | 10D | 10D | 10D | 9BS | 9.5BS | 10D | 9.8RS |
| Control | 0 | 0 | 0 | 0 | 0 | 0 | 0 | 0 | 0 | 0 | 0 | 0 | 0 | 0 | 0 |

TABLE XIII
COMBINATION OF 1-METHOXY-6-CHLORO-2-TRIFLUOROMETHYL-1H-IMIDAZO(4,5-b)PYRIDINE ("A") WITH LINURON ("B")

| Compounds | Rates Lbs./Acre | Morning Glory | Corn | Foxtail Millet | Ragweed | Barnyard Grass | Large Crabgrass | Digweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.25 | 2SBC | 2SB | 8BS | 10D | 4BS | 5S | 9SB | 0 | 2B | 9BS | 0 | 8BS | 2SB | 9.5RS |
| " | 0.25 + 0.5 | 3SB | 0 | 8BS | 7BS | 8BS | 5S | 9SB | 0 | 2B | 10D | 0 | 8BS | 9BS | 10D |
| " | 0.25 + 1.0 | 4SB | 0 | 10D | 9BS | 10D | 9BS | 10D | 3BS | 4B | 10D | 0 | 9BS | 9BS | 9SR |
| " | 0.25 + 2.0 | 9BS | 3S | 10D | 10D | 9.5BS | 9BS | 9S | 4SB | 4B | 10D | 4BS | 8BS | 9BS | 8SR |
| " | 0.5 + 0.25 | 10D | 3B | 8BS | 8BS | 8BS | 7SB | 9BS | 3B | 3B | 9BS | 1S | 9BS | 7BS | 9SRB |
| " | 0.5 + 0.5 | 5SB | 0 | 8BS | 9BS | 9BS | 7BS | 10D | 2S | 2B | 10D | 0 | 9BS | 9BS | 9SR |
| " | 0.5 + 1.0 | 9BS | 0 | 10D | 9BS | 9BS | 8BS | 9S | 3S | 3B | 10D | 2S | 8BS | 8BS | 9SR |
| " | 0.5 + 2.0 | 10D | 3S | 10D | 10D | 10D | 9.5BS | 9.5BS | 3SB | 4B | 10D | 3S | 9BS | 9.5BS | 9SR |
| " | 1.0 + 0.25 | 10D | 2S | 10D | 10D | 9.5BS | 9.5BS | 9.5BS | 4SB | 3B | 9.5BS | 2S | 9.5BS | 9.5BS | 9SR |
| " | 1.0 +0.5 | 10D | 3S | 10D | 10D | 9BS | 9.5BS | 9.5BS | 8B | 4B | 10D | 3S | 9.5BS | 10D | 9.5RS |
| " | 1.0 + 1.0 | 10D | 4SB | 10D | 10D | 9.5BS | 9.5BS | 9BS | 5B | 10D | 3S | 9.5BS | 9.5BS | 9.5RS |
| " | 1.0 + 2.0 | 10D | 6SB | 10D | 10D | 9.5BS | 9.5BS | 9.5BS | 6B | 10D | 5SB | 9.5BS | 10D | 10D |
| " | 2.0 + 0.25 | 10D | 5S | 10D | 10D | 9.5BS | 9.5BS | 9.5BS | 9B | 10D | 5SB | 10D | 10D | 9.5RS |
| " | 2.0 + 0.5 | 10D | 5SB | 10D | 10D | 9.5BS | 9.5BS | 9.5BS | 8B | 10D | 7SB | 9.5BS | 9.5BS | 9.5RS |
| " | 2.0 + 1.0 | 10D | 6SB | 10D | 10D | 9.5BS | 10D | 9B | 8B | 10D | 5SB | 9.5BS | 9.5BS | 9.5RS |
| " | 2.0 + 2.0 | 10D | 7SB | 10D | 10D | 9.5BS | 9.5BS | 10D | 9BS | 10D | 6SB | 10D | 10D | 9.5RS |

TABLE XIII-continued
COMBINATION OF 1-METHOXY-6-CHLORO-2-TRIFLUOROMETHYL-1H-IMIDAZO(4,5-b)PYRIDINE ("A") WITH LINURON ("B")

| Compounds | Rates Lbs./Acre | Morning Glory | Corn | Foxtail Millet | Ragweed | Barnyard Grass | Large Crabgrass | Digweed | Sorghum | Rice | Velvet Leaf | Corn | Jimson Weed | Johnson Grass | Lambs Quarter |
|---|---|---|---|---|---|---|---|---|---|---|---|---|---|---|---|
| Control | 0 | 0 | 0 | 0 | 0 | 0 | 0 | 0 | 0 | 0 | 0 | 0 | 0 | 0 | 0 |

TABLE XIV
COMBINATION OF 1-METHOXY-6-CHLORO-2-TRIFLUOROMETHYL-1H-IMIDAZO(4,5-b)PYRIDINE ("A") WITH ORYZALIN ("B")

| Compounds | Rates Lbs./Acre | | Morning Glory | Pigweed | Ragweed | Corn | Velvet Leaf | Lambs Quarter | Jimson Weed | Barnyard Grass | Rice | Large Crabgrass | Corn | Foxtail Millet | Sorghum | Johnson Grass |
|---|---|---|---|---|---|---|---|---|---|---|---|---|---|---|---|---|
| A+B | ¼ | ¼ | 5S | 6S | 5S | 6.5 BS | 5.5CS | 10N | 3CS | 7RS | 6.5 CS | 9.5RS | 5CS | 8.5SD | 7BS | 6.5BS |
| " | ¼ | 1 | 5S | 7.5RS | 6.5 CRS | 7.5 BS | 6CS | 9.5RS | 6S | 8.5RS | 8CS | 9.5RS | 7BS | 9SD | 7.5BS | 7BS |
| " | ¼ | 2 | 9BSD | 9RS | 8RS | 8BS | 7CS | 10N | 6.5S | 9RS | 8CS | 10N | 8BS | 9.5RS | 8BPS | 8BSD |
| " | ¼ | 4 | 9.5 BSD | 9RS | 8.5RS | 9BS | 9BS | 10N | 7BS | 9.5RS | 9BS | 10N | 9BS | 10D | 9BS | 8.5 BSD |
| " | ½ | ¼ | 8BSD | 8RS | 8.5 BSD | 6BS | 5CBS | 9a.5RS | 5S | 6.5RS | 6.5 CS | 9RS | 5BS | 9BSD | 6.5RS | 7BSD |
| " | ½ | 1 | 9.5 BSD | 9.5RS | 9BS | 7BS | 6.5BS | 10N | 9BSD | 9RS | 7.5 BSC | 10N | 7BS | 10D | 7BS | 8SD |
| " | ½ | 2 | 9.5 BSD | 9.5RS | 9BSD | 7BS | 8.5BSD | 10N | 8BSD | 9.5RS | 8.5 BS | 10N | 8BS | 9.5SD | 8.5BS | 8BSD |
| " | ½ | 4 | 10D | 9.5RS | 9.5SD | 8BS | 8.5BSD | 10N | 9BSD | 10D | 8.5 BS | 10N | 7.5 BS | 10D | 9BS | 8BSD |
| " | 1 | ;178 | 10D | 9RS | 9.5SD | 4S | 6BSD | 9.5RS | 9.5BSD | 9SD | 7BS | 9.5SD | 4S | 10D | 7BS | 9BSD |
| " | 1 | 1 | 10D | 9RS | 9.5SD | 7BS | 7BSD | 10N | 9.5BSD | 9SD | 7BS | 9.5RS | 6S | 9SD | 5BS | 9BSD |
| " | 1 | 2 | 9.5 BSD | 10N | 9.5 BSD | 7BS | 9.5BSD | 10N | 9BSD | 10D | 8BS | 10N | 7.5 BS | 10D | 9SD | 9.5SD |
| " | 1 | 4 | 10D | 10N | 10D | 7BS | 9.5BSD | 10N | 9.5BSD | 10D | 8.5 BS | 10N | 8.5 BS | 10D | 9BSD | 9.5 BSD |
| " | 2 | ¼ | 10D | 9.5RS | 9.5SD | 2.5 BS | 10D | 10N | 9.5SD | 9.5RS | 7SD | 10N | 3S | 10D | 7BS | 10D |
| " | 2 | 1 | 10D | 9.5SD | 9.5SD | 4BS | 10D | 9.5RS | 9.5SD | 10D | 8 BSD | 10N | 4.5 BS | 10D | 7.5 BSD | 10D |
| " | 2 | 2 | 10D | 10N | 9.5SD | 6.5 BS | 10D | 10N | 10D | 10D | 8 BSD | 9.5SD | 5.5S | 10D | 7.5 BSD | 9.5SD |
| " | 2 | 4 | 9.5SD | 10D | 10D | 3.5S | 9.5SD | 10N | 10D | 10D | 6.5 BS | 10N | 5.5S | 10D | 8.5 BSD | 10D |
| Control | — | — | 0 | 0 | 0 | 0 | 0 | 0 | 0 | 0 | 0 | 0 | 0 | 0 | 0 | 0 |

TABLE XV:
COMBINATION OF 1-METHOXY-6-CHLORO-2-TRIFLUOROMETHYL-1H-IMIDAZO(4,5-6)PYRIDINE ("A") WITH PROPACHLOR ("B")

| Compounds | Rates Lbs./Acre | Morning Glory | Corn | Foxtail Millet | Ragweed | Barnyard Grass | Large Crabgrass | Pigweed | sorghum | Rice | Velvet Leaf | Corn | Jimson Weed | Johnson Grass | Lambs Quarter |
|---|---|---|---|---|---|---|---|---|---|---|---|---|---|---|---|
| A+B | 0.25 + 1.0 | 7BS | 0 | 10D | 10D | 9RS | 8RS | 10D | 2B | 9RS | 6SB | 0 | 10D | 4SR | 7RS |
| " | 0.25 + 2.0 | 10D | 0 | 10D | 10D | 9RS | 8RS | 5SB | 3SB | 9RS | 7BS | 0 | 9BS | 3S | 6RS |
| " | 0.25- + 3.0 | 9BS | 0 | 10D | 10D | 9RS | 10D | 10D | 4S | 10N | 9BSR | 0 | 9BS | 4S | 7S |
| " | 0.25 + 4.0 | 10D | 1S | 10D | 10D | 9RS | 8S | 7SR | 4S | 10N | 9BS | 0 | 8BS | 4S | 7S |
| " | 0.5 + 1.0 | 9BS | 0 | 10D | 10D | 8RSB | 8S | 7RS | 3BS | 8BS | 8BS | 0 | 8BS | 5SB | 8SB |
| " | 0.5 + 2.0 | 10D | 0 | 10D | 10D | 9BSR | 8S | 8SR | 2SB | 9RS | 9BS | 0 | 9BS | 6SB | 8SR |
| " | 0.5 + 3.0 | 10D | 0 | 10D | 10D | 9BSR | 8SR | 8SR | 4S | 9RS | 9BS | 0 | 9BS | 5S | 7S |
| " | 0.5 + 4.0 | 10D | 0 | 10D | 10D | 10D | 10N | 10N | 4S | 9RS | 9BS | 2S | 9BS | 6SB | 8S |
| " | 1.0 + 1.0 | 10D | 0 | 10D | 10D | 10D | 10N | 10D | 6BS | 5SB | 9BS | 0 | 9BS | 9BS | 9RS |
| " | 1.0 + 2.0 | 10D | 2S | 10D | 10D | 10D | 9.5RS | 10N | 5BS | 5SB | 9BS | 0 | 10D | 9.5BS | 8SR |
| " | 1.0 + 3.0 | 10D | 0 | 10D | 10D | 9BSR | 9RS | 9BSR | 6BS | 9RS | 10D | 1S | 9BS | 9.5BS | 8S |

TABLE XV:-continued

COMBINATION OF 1-METHOXY-6-CHLORO-2-TRIFLUOROMETHYL-1H-IMIDAZO(4,5-6)PYRIDINE ("A") WITH PROPACHLOR ("B")

| Compounds | Rates Lbs./Acre | Morning Glory | Corn | Foxtail Millet | Ragweed | Barnyard Grass | Large Crabgrass | Pigweed | sorghum | Rice | Velvet Leaf | Corn | Jimson Weed | Johnson Grass | Lambs Quarter |
|---|---|---|---|---|---|---|---|---|---|---|---|---|---|---|---|
| " | 1.0 + 4.0 | 10D | 0 | 10D | 10D | 10D | 10N | 10N | 4SB | 9RS | 10D | 0 | 9BS | 9.5BS | 9SR |
| " | 2.0 + 1.0 | 10D | 3S | 10D | 10D | 10D | 10D | 10D | 9BS | 7BS | 10D | 3S | 9BS | 9BS | 9RS |
| " | 2.0 + 2.0 | 10D | 4S | 10D | 10D | 10D | 10D | 9SR | 8BS | 9RS | 10D | 5SB | 9BS | 10D | 9S |
| " | 2.0 + 3.0 | 10D | 3S | 10D | 10D | 10D | 10N | 10N | 9BS | 8RS | 10D | 4S | 9BS | 10D | 9SR |
| " | 2.0 + 4.0 | 10D | 1S | 10D | 10D | 10D | 10D | 9.8BSR 9BS | 10N | 10D | 3S | 10D | 10D | 10N | |
| Control | 0 | 0 | 0 | 0 | 0 | 0 | 0 | 0 | 0 | 0 | 0 | 0 | 0 | 0 | 0 |

TABLE XVI:

COMBINATION OF 1-METHOXY-6-CHLORO-2-TRIFLUOROMETHYL-1H-IMIDAZO(4,5-b)PEPIDINE ("A") WITH PROPAZINE ("B")

| Compounds | Rates Lbs./Acre | | Morning Glory | Pigweed | Ragweed | Sorghum | Velvet Leaf | Lambs Quarter | Jimson Weed | Barnyard Grass | Rice | Large Crabgrass | Sorghum | Foxtail Millet | Corn | Johnson Grass |
|---|---|---|---|---|---|---|---|---|---|---|---|---|---|---|---|---|
| A + B | ½ | ¾ | 8DS | 8SD | 8BSD | 0 | 3BSD | 9RSD | 9.5SD | 5SD | 2BS | 3S | 0 | 6 BSD | 0 | 8BSD |
| " | ½ | 1½ | 8.5 BSD | 8SD | 9BSD | 0 | 5BSD | 9RSD | 9BSD | 4SD | 3BS | 4.5RS | 0 | 7 BSD | 0 | 7BSD |
| " | ½ | 3 | 8.5 BSD | 8.5SD | 9BSD | 0 | 3CS | 8RSD | 9.5BSD | 8BSD | 5BS | 7.5 RSD | 0 | 6 BSD | 0 | 7.5BSD |
| " | 1 | ¾ | 10D | 8.5SD | 9BSD | 3BS | 7.5 BSD | 8RSD | 9.5SD | 7BSD | 1BS | 9RSD | 0 | 9.5 SD | 2S | 9.5BSD |
| " | 1 | 1½ | 10D | 8SD | 9.5 BSD | 3BS | 10D | 9RSD | 9.5 BSD | 8.5 BSD | 2BS | 8RSD | 2BS | 10D | 0 | 9.5BSD |
| " | 1 | 3 | 10D | 8.5SD | 10D | 2BS | 10D | 9RSD | 9.5 BSD | 9.5 BSD | 4BS | 9RSD | 1BS | 9SD | 0 | 9.5BSD |
| " | 1½ | ¾ | 10D | 8SD | 8BSD | 2BS | 8BSD | 9RSD | 9.5SD | 10D | 6BSD | 9.5 RSD | 2BS | 10D | 0 | 10D |
| " | 1½ | 1½ | 9.5 BSD | 8BSD | 10D | 2.5BS | 9.5 BSD | 9RSD | 9.5 BSD | 9BSD | 5BSD | 10D | 2BS | 10D | 2BS | 9.5BSD |
| " | 1½ | 3 | 10D | 8BSD | 10D | 3BS | 10D | 9RSD | 10D | 9.5 BSD | 7BSD | 8SD | 3.5BS | 10D | 1S | 9.5BSD |
| " | 2 | ¾ | 10D | 8BSD | 9BSD | 3BS | 9.5 BSD | 9RSD | 9.5 BSD | 9.5 BSD | 5BSD | 9.5SD | 4BS | 10D | 2S | 10D |
| " | 2 | 1½ | 10D | 8BSD | 9.5 BSD | 2BS | 10D | 9.5 RSD | 10D | 10D | 6.5 BSD | 10D | 3BS | 10D | 1S | 9BSD |
| " | 2 | 3 | 10D | 8.5 BSD | 10D | 2BS | 9BSD | 9.5 RSD | 9.5 BSD | 10D | 6BSD | 9RSD | 2BS | 10D | 0 | 10D |
| Control | — | — | 0 | 0 | 0 | 0 | 0 | 0 | 0 | 0 | 0 | 0 | 0 | 0 | 0 |
| Control | — | — | 0 | 0 | 0 | 0 | 0 | 0 | 0 | 0 | 0 | 0 | 0 | 0 | 0 |
| Control | — | — | 0 | 0 | 0 | 0 | 0 | 0 | 0 | 0 | 0 | 0 | 0 | 0 | 0 |

TABLE XVII:

COMBINATION OF 1-METHOXY-6-CHLORO-2-TRIFLUOROMETHYL-1H-IMIDAZO(4,5-b)PYRIDINE ("A") WITH SIMAZINE ("B")

| Compounds | Rates Lbs./Acre | | Morning Glory | Pigweed | Ragweed | Corn | Velvet Leaf | Lambs Quarter | Jimson Weed | Barnyard Grass | Rice | Large Crabgrass | Corn | Foxtail millet | Sorghum | Johnson Grass |
|---|---|---|---|---|---|---|---|---|---|---|---|---|---|---|---|---|
| A+B | ¼ | ¼ | 6.5 BSD | 8.5BS | 6.5SD | 0 | 2S | 6.5S | 9.5SD | 0 | 1BS | 6BS | 0 | 4.5BS | 0 | 4BS |
| " | ¼ | ½ | 10D | 7BSD | 7RSD | 0 | 5CS | 10D | 10D | 6BSD | 2BS | 7.5BS | 0 | 6BS | 0 | 7BSD |
| " | ¼ | 1 | 10D | 8.5 BSO | 9SD | 0 | 6CS | 9SD | 9.5SD | 8BSD | 2BS | 9BSD | 0 | 7BSD | 0 | 9BSD |
| " | ¼ | 2 | 10D | 8.5 BSD | 9SD | 0 | 8SD | 9.5SD | 10D | 9.5 BSD | 3BS | 9BSD | 6BSD | 9.5 BSD | 2S | 9BSD |
| " | ½ | ¼ | 10D | 8BS | 8BSD | 0 | 5CS | 9BSD | 9SD | 3BS | 1B | 6SD | 0 | 7.5 BSD | 0 | 8.5 BSD |
| " | ½ | ½ | 9.5 BSD | 8.5BS | 9.5SD | 0 | 6.5 BSD | 9BSD | 9.5SD | 3BS | 6.5BS | 8SD | 0 | 8BSD | 0 | 9BSD |
| " | ½ | 1 | 9.5 BSD | 9BS | 9.5SD | 0 | 6.5 BSD | 10D | 10D | 3.5BS | 5BS | 9SD | 0 | 9.5 BSD | 0 | 9.5 BSD |
| " | ½ | 2 | 10D | 9.5BS | 10D | 0 | 7CSD | 10D | 10D | 9.5BS | 5BS | 9.5SD | 0 | 10D | 4BS | 9.5 BSD |
| " | 1 | ¼ | 9.5 BSD | 9BS | 9SD | 0 | 7SD | 9BS | 10D | 7BSD | 3BS | 9BSD | 0 | 9BSD | 0 | 10D |
| " | 1 | ½ | 10D | 6.5BS | 9SD | 1S | 6SD | 9BS | 9.5 BSD | 9.5 BSD | 2BS | 9.5 BSD | 1.5S | 9.5 BSD | 3BS | 10D |
| " | 1 | 1 | 10D | 8S | 10D | 0 | 7SD | 7.5BS | 9.5 | 9.5 | 6BS | 10D | 0 | 9.5 | 3BS | 10D |

TABLE XVII:-continued
COMBINATION OF 1-METHOXY-6-CHLORO-2-TRIFLUOROMETHYL-1H-IMIDAZO(4,5-b)PYRIDINE ("A") WITH SIMAZINE ("B")

| Compounds | Rates Lbs./Acre | | Morning Glory | Pigweed | Ragweed | Corn | Velvet Leaf | Lambs Quarter | Jimson Weed | Barnyard Grass | Rice | Large Crabgrass | Corn | Foxtail millet | Sorghum | Johnson Grass |
|---|---|---|---|---|---|---|---|---|---|---|---|---|---|---|---|---|
| " | 1 | 2 | 10D | 9.5BS | 8SD | 1S | 9SD | 10D | 10D | BSD 9BSD | 4BS | 10D | BSD 1.5S | 10D | 5BS | 10D |
| " | 2 | ¼ | 10D | 9BSD | 9.5 BSD | 1.5S | 10D | 10D | 10D | BSD 9BSD | 6BSD | 9.5 BSD | 0 | 10D | 3BS | 10D |
| " | 2 | ½ | 10D | 9.5 BSD | 9.5 BSD | 2S | 9.5 BSD | 9BS | 9.5SD | 9BSD | 6BSD | 9.5 BSD | 1.5S | 10D | 5BS | 9.5 BSD |
| " | 2 | 1 | 10D | 9.5 BSD | 9.5 BSD | 1S | 9BSD | 9.5BS | 10D | 9.5 BSD | 6BSD | 10D | 1S | 10D | 4.5BS | 9.5 BSD |
| " | 2 | 2 | 9.5 BSD | 9BSD | 9.5 BSD | 1.5S | 9.5 BSD | 10D | 10D | 9.5 BSD | 6BSD | 10D | 1S | 10D | 6BS | 9.5 BSD |
| Control | — | — | 0 | 0 | 0 | 0 | 0 | 0 | 0 | 0 | 0 | 0 | 0 | 0 | 0 | 0 |

TABLE XVIII
COMBINATION OF 1-METHOXY-6-CHLORO-2-TRIFLUOROMETHYL-1H-IMIDAZO(4,5-b)PYRIDINE ("A") WITH TRIFLURALIN ("B")

| Compounds | Rates Lbs./Acre | | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|---|
| A + B | 0.21 | 0.25 | 6SB | 0 | 9SR | 10N | 9SR | 10N | 10N | 7SR | 5SC | 0 | 0 | 2S | 5SR | 4S |
| " | " | 0.5 | 8SB | 0 | 9SR | 10D | 9RS | 9.5RS | 10N | 7SR | 6SC | 3SB | 0 | 5SB | 4S | 5S |
| " | " | 1.0 | 10D | 0 | 9BSR | 10D | 9RSB | 9.5RS | 9.5 BS | 9SR | 5SCB | 8BS | 2S | 8BS | 9.5RS | 9BSR |
| " | " | 2.0 | 10D | 5S | 10N | 10D | 9.5RS | 9.5RS | 10N | 8SR | 5SB | 10D | 4S | 9BSR | 10N | 10N |
| " | 0.42 | 0.25 | 5SB | 4S | 9RSB | 5SB | 10N | 10N | 10N | 10N | 8SC | 2S | 4SC | 2SC | 9.5RS | 6SR |
| " | " | 0.5 | 6BS | 5S | 9.8RS | 10D | 9.5RS | 9.5RS | 10N | 10N | 9SC | 3S | 4S | 5SB | 10N | 8SR |
| " | " | 1.0 | 10D | 4S | 9.8RS | 10D | 10N | 10N | 10N | 9.8RS | 8SC | 10D | 5SB | 9BS | 9.5RS | 9RS |
| " | " | 2.0 | 10D | 5S | 10N | 10D | 10N | 10N | 10N | 10N | 8SCR | 10D | 5SC | 9BS | 9.5RS | 10N |
| " | 0.83 | 0.25 | 6SB | 7 FSC | 10N | 7RS | 9.5RS | 10N | 10N | 10N | 9CSR | 3S | 7CSF | 3S | 9.5RS | 8RS |
| " | " | 0.5 | 7BS | 8 RSF | 10N | 10D | 10N | 10N | 10N | 9.9RS | 9CSR | 4SB | 7CSF | 8BSF | 9.8RS | 9.5RS |
| " | " | 1.0 | 8SB | 8 BSF | 9.8RS | 10D | 9.8RS | 10N | 10N | 10N | 9SRF | 7BS | 7SC | 9.5BS | 9.9RS | 9.5RS |
| " | " | 2.0 | 9BS | 8 SCB | 10N | 10D | 10N | 10N | 10N | 10N | 9SCR | 9.8BS | 7SCB | 9BSF | 10N | 9.5RS |
| " | 2.0 | 0.25 | 7SB | 9 RSF | 10N | 8 BSR | 10N | 10N | 10N | 10N | 9.5SR | 6S | 9RSF | 4SB | 10N | 10N |
| " | " | 0.5 | 7SB | 9 RSB | 10N | 9.5 BS | 10N | 10N | 10N | 10N | 9.8RS | 5SF | 8FSB | 6SF | 10N | 10N |
| " | " | 1.0 | 10D | 9 FSB | 10N | 10D | 10N | 10N | 8SR | 10N | 9RS | 10D | 9SF | 9.5BS | 10N | 9.5RS |
| " | " | 2.0 | 10D | 9 FSB | 10N | 10D | 10N | 10N | 9.5 RS | 10N | 9.5SR | 9.5BS | 9FSB | 10D | 10N | 10N |
| Control | 0 | 0 | 0 | 0 | 0 | 0 | 0 | 0 | 0 | 0 | 0 | 0 | 0 | 0 | 0 | 0 |

TABLE XIX
COMBINATION OF 1-METHOXY-6-CHLORO-2-TRIFLUOROMETHYL-1H-IMIDAZO(4,5-b)PYRIDINE ("A") WITH TCA ("B")

| Compounds | Rates Lbs./Acre | | Morning Glory | Pigweed | Ragweed | Corn | Velvet Leaf | Lambs Quarter | Jimson Weed | Barnyard Grass Rice | grass | Large Crabgrass Corn | Millet | Foxtail Sorghum | Grass | Johnson |
|---|---|---|---|---|---|---|---|---|---|---|---|---|---|---|---|---|
| A + B | ¼ | ¾ | 2CS | — | — | 1S | 0 | 0 | 2.5S | 1S | 0 | 1S | 0 | 4BFD | 0 | 3BS |
| " | ¼ | 1½ | 2CS | — | — | 2S | 0 | 2S | 4S | 0 | 5BS | 8SD | 0 | 7BFD | 0 | 3BS |
| " | ¼ | 3 | 2CS | — | — | 1S | 0 | 3RS | 2S | 2S | 9BSD | 9BSD | 0 | 9BFD | 0 | 4BS |
| " | ¼ | 6 | 1C | — | — | 1S | 0 | 3S | 3S | 7BFS | 10D | 7BSD | 0 | 9.5BFD | 7BFD | 8BSD |
| " | ½ | ¾ | 3BS | — | — | 0 | 0 | 2S | 7BSD | 3S | 6BSD | 5BS | 0 | 8.5BSD | 0 | 4BS |
| " | ½ | 1½ | 5BS | — | — | 0 | 4CS | 3S | 6BSD | 4BS | 5BS | 3BS | 0 | 7BSD | 0 | 8BSD |
| " | ½ | 3 | 4BSD | — | — | 0 | 5CBS | 8RS | 10D | 8BSD | 8BS | 5SD | 0 | 7BFSD | 3BFS | 9BSD |
| " | ½ | 6 | 7BSD | — | — | 3FS | 6BSD | 8RSD | 9BSD | 6BSD | 8BSD | 7BSD | 2FS | 9.5BSD | 8BFSD | 9BSD |
| " | 1 | ¾ | 9BSD | — | — | 0 | 7BSD | 7RS | 9BSD | 7BSD | 3BS | 6BSD | 1S | 8BSD | 0 | 8BSD |
| " | 1 | 1½ | 9BSD | — | — | 0 | 5BS | 7RS | 9.5 BSD | 9BSD | 8.5 BSD | 9BSD | 1.5S | 9BSD | 3BS | 9BSD |
| " | 1 | 3 | 5CBS | — | — | 0 | 6CBS | 4RS | 9BSD | 6BSD | 7BSD | 9BSD | 2S | 10D | 3BS | 8BSD |
| " | 1 | 6 | 6 BCSD | — | — | 1S | 8BSD | 8RS | 9BSD | 9BSD | 9BSD | 9BSD | 0 | 9.5BSD | 6BFS | 10D |
| " | 2 | ¾ | 10D | — | — | 2S | 9BSD | 7RS | 9.5 BSD | 9.5 BSD | 6BSD | 8BSD | 1S | 7BSD | 3BS | 9BSD |
| " | 2 | 1½ | 10D | — | — | 1S | 9BSD | 7RS | 9.5 BSD | 9.5 BSD | 6BSD | 10D | 2S | 10D | 3BS | 9.5BSD |
| " | 2 | 3 | 10D | — | — | 3S | 9BSD | 8RS | 9BSD | 9.5 BSD | 7BSD | 8BSD | 0 | 10D | 6BSD | 9.5BSD |
| " | 2 | 6 | 10D | — | — | 4FS | 10D | 9RS | 9BSD | 9.5 BSD | 9BSD | 8.5 BSD | 3FS | 10D | 8.5BSFD | 10D |
| Control | — | — | 0 | — | — | 0 | 0 | 0 | 0 | 0 | 0 | 0 | 0 | 0 | 0 | 0 |

EXAMPLES 104-107

Additional evaluations were conducted, in accordance with the procedures of the foregoing examples, with 1-methoxy-5-chloro-2-trifluoromethyl-1H-imidazo(4,5-b)pyridine and with 1-methoxy-2,6-bis(trifluoromethyl)-1H-imidazo(4,5-)pyridine. Each was employed in combination with alachlor and separately in combination with atrazine. The results were as set forth in the following tables.

TABLE XX: COMBINATION OF 1-METHOXY-5-CHLORO-2-TRIFLUOROMETHYL-1H-IMIDAZO(4,5-b)PYRIDINE ("A") WITH ALACHLOR ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.5 | 3SE | 2S | 9.5BS | 9.5RS | 9.5RS | 10D | 9.5RS | 9RSF | 9RS | 9.5 BS | 0 | 9BS | 9RSB | 10D |
| " | 0.25 + 1.0 | 4SE | 0 | 10D | 10D | 10D | 10D | 10D | 9RSF | 9.8RS | 8BS | 0 | 9.5-BS | 9RSB | 10D |
| " | 0.25 + 2.0 | 6BSC | 2S | 10N | 10N | 10D | 10N | 10N | 9.5BS | 10N | 9BS | 1S | 10D | 9.5BS | 10N |
| " | 0.25 + 4.0 | 9.5BS | 0 | 10D | 10D | 10N | 10N | 10N | 9.5BS | 10N | 9.5BS | 3S | 10D | 10D | 10D |
| " | 0.5 + 0.5 | 9.5BS | 2BS | 10D | 9RS | 9RSB | 9.5RS | 10N | 8SFB | 9.5RS | 10D | 2S | 10D | 8RSB | 9.5RS |
| " | 0.5 + 1.0 | 9BS | 0 | 10D | 10D | 9.5RS | 10D | 10N | 9.5BS | 10N | 10D | 0 | 10D | 8BSR | 9RS |
| " | 0.5 + 2.0 | 10D | 2S | 10D | 10D | 10D | 10N | 10N | 9.8BS | 10N | 10D | 2S | 10D | 9.5RSB | 9.5BS |
| " | 0.5 + 4.0 | 10D | 0 | 10N | 10D | 10N | 10N | 10N | 10D | 10N | 10D | 2S | 10D | 10D | 10D |
| " | 1.0 + 0.5 | 10D | 0 | 10D | 10D | 10D | 10N | 10D | 9.8BS | 9.5RS | 10D | 1S | 10D | 8RSB | 10D |
| " | 1.0 + 1.0 | 10D | 2S | 10D | 10D | 10N | 10N | 9.5RS | 8BSF | 10D | 10D | 0 | 10D | 9.5BS | 9.5RS |
| " | 1.0 + 2.0 | 10D | 1S | 10D | 10D | 10N | 10N | 10N | 9.8BS | 10N | 10D | 2S | 10D | 9.5BS | 10N |
| " | 1.0 + 4.0 | 9.8BS | 2SB | 10N | 10N | 10N | 10N | 10N | 9.8BS | 10N | 10D | 2SB | 10D | 10D | 10D |
| " | 2.0 + 0.5 | 10D | 0 | 10D | 10D | 10D | 10D | 10D | 9BSF | 9RSB | 10D | 0 | 10D | 9BSR | 10D |
| " | 2.0 + 1.0 | 10D | 2S | 10D | 10D | 10N | 10N | 10N | 10D | 8RSB | 10D | 0 | 10D | 10D | 10D |
| " | 2.0 + 2.0 | 10D | 3S | 10N | 10D | 10N | 10N | 10N | 10D | 10N | 10D | 4SB | 9BSR | 9.5RS | 10D |
| " | 2.0 + 4.0 | 10D | 3S | 10D | 10D | 10N | 10N | 10N | 10D | 10N | 10D | 2S | 10D | 9.5BS | 10N |
| Control | 0 | 0 | 0 | 0 | 0 | 0 | 0 | 0 | 0 | 0 | 0 | 0 | 0 | 0 | 0 |

TABLE XXI: COMBINATION OF 1-METHOXY-5-CHLORO-2-TRIFLUOROMETHYL-1H-IMIDAZO(4,5-b)PYRIDINE ("A") WITH ATRAZINE ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.25 | 7BS | 1S | 7BS | 10D | 6SB | 4SB | 6SB | 0 | 5B | 8BS | 0 | 10D | 0 | 7SB |
| " | 0.25 + 0.5 | 8BS | 0 | 7BS | 10D | 5SB | 3SB | 7SB | 0 | 5B | 9BS | 0 | 9BS | 0 | 7SB |
| " | 0.25 + 1.0 | 10D | 0 | 8BS | 10D | 9BS | 8BS | 8BS | 0 | 5B | 10D | 0 | 10D | 2S | 8BS |
| " | 0.25 + 2.0 | 10D | 0 | 9BS | 10D | 8BS | 7BS | 7BS | 0 | 9B | 10D | 0 | 10D | 2SB | 9BS |
| " | 0.5 + 0.25 | 9BS | 0 | 9BS | 10D | 7SB | 8BS | 8BS | 0 | 8B | 10D | 0 | 10D | 3SB | 8BS |
| " | 0.5 + 0.5 | 10D | 0 | 10D | 10D | 7BS | 5SB | 8BS | 1S | 6B | 7.5BS | 0 | 10D | 3SB | 9BS |
| " | 0.5 + 1.0 | 10D | 2C | 9.5BS | 10D | 7BS | 6BS | 8BS | 2S | 5B | 10D | 3SC | 9BS | 3SC | 10D |
| " | 0.5 + 2.0 | 10D | 0 | 9.5BS | 10D | 9BS | 7BS | 9BS | 1S | 9B | 10D | 0 | 10D | 3S | 9BS |
| " | 1.0 + 0.25 | 10D | 1S | 9.5BS | 10D | 9BS | 6BS | 9BS | 2S | 8B | 10D | 0 | 10D | 3S | 9BS |
| " | 1.0 + 0.5 | 10D | 2SB | 10D | 10D | 9.5BS | 7SB | 8BS | 3SB | 9B | 10D | 0 | 10D | 4SB | 9BS |
| " | 1.0 + 1.0 | 10D | 1SB | 10D | 10D | 9.5BS | 9BS | 9BS | 3SB | 10D | 10D | 0 | 10D | 4SB | 9BS |
| " | 1.0 + 2.0 | 10D | 3S | 10D | 10D | 9BS | 7BS | 9BS | 5SB | 10D | 10D | 1S | 10D | 3SB | 9BS |
| " | 2.0 + 0.25 | 10D | 4SB | 10D | 10D | 9.5BS | 8BS | 9BS | 8BS | 10D | 10D | 3SB | 10D | 9BS | 9BS |
| " | 2.0 + 0.5 | 10D | 4SB | 10D | 10D | 9.5BS | 9.5BS | 9.5BS | 8BS | 9.5BS | 10D | 3S | 10D | 5SB | 9BS |
| " | 2.0 + 1.0 | 10D | 6SB | 10D | 10D | 9BS | 9.5BS | 9.5BS | 8BS | 10D | 10D | 2S | 10D | 5SB | 10D |
| " | 2.0 + 2.0 | 10D | 3S | 10D | 10D | 10D | 9.8BS | 9.5BS | 8SB | 9B | 10D | 3S | 10D | 6SB | 9BS |
| Control | 0 | 0 | 0 | 0 | 0 | 0 | 0 | 0 | 0 | 0 | 0 | 0 | 0 | 0 | 0 |

TABLE XXII: COMBINATION OF 1-METHOXY-2,6-BIS(TRIFLUOROMETHYL)-1H-IMIDAZO(4,5-b)PYRIDINE ("A") WITH ALACHLOR ("B")

| Compounds | Rates Lbs./Acre | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|
| A + B | 0.25 + 0.5 | 2E | 0 | 9.5BS | 4SB | 9RS | 7RSB | 8BSR | 1S | 5RB | 4SB | 0 | 3SB | 4SR | 9RS |
| " | 0.25 + 1.0 | 3SFE | 0 | 10D | 6SB | 9.5RS | 10D | 10D | 5SF | 8RS | 5SB | 0 | 5SB | 7RS | 9RS |
| " | 0.25 + 2.0 | 5SEF | 0 | 10D | 9.5BS | 10N | 10D | 10N | 5SF | 9RS | 5SB | 0 | 6SB | 9RS | 9RSB |
| " | 0.25 + 4.0 | 7SBF | 3SF | 10N | 9.5RS | 10D | 10D | 10D | 7SFB | 10N | 8SB | 2S | 8BS | 10D | 10N |
| " | 0.5 + 0.5 | 5SBF | 0 | 10D | 5SB | 9RS | 8RSB | 10D | 3SB | 7SRB | 7BS | 0 | 8BS | 7RSF | 8SR |
| " | 0.5 + 1.0 | 6SBF | 0 | 10D | 7SR | 9.5RS | 10D | 10D | 3SF | 9RSB | 9.5BS | 0 | 9BS | 7RSB | 9BSR |
| " | 0.5 + 2.0 | 9.5BS | 1S | 10D | 10N | 10D | 10N | 10N | 8BSF | 9.5RS | 9BS | 1S | 9BS | 9.5BS | 10N |
| " | 0.5 + 4.0 | 9.5BS | 3S | 10D | 10D | 10D | 10D | 10D | 9.5BS | 10N | 9BS | 4SF | 10D | 9.5BS | 10N |
| " | 1.0 + 0.5 | 9.5BS | 0 | 10D | 6S | 7SR | 8RSB | 10D | 4SFB | 4S | 9BS | 0 | 9BS | 8BS | 9RS |
| " | 1.0 + 1.0 | 8BS | 0 | 10D | 7RS | 9RS | 9RSB | 10D | 8BSF | 9RS | 9BS | 0 | 9.5BS | 9.5BS | 9.5RS |
| " | 1.0 + 2.0 | 9.5BS | 3SB | 10N | 8RS | 10D | 10D | 10N | 8RSB | 10N | 9.5BS | 3S | 9.5BS | 9.5RS | 9.5RS |
| " | 1.0 + 4.0 | 10N | 0 | 10N | 9SR | 10N | 10N | 10D | 9.5RS | 10N | 9BS | 3S | 9BS | 10D | 9.5RS |
| " | 2.0 + 0.5 | 10D | 0 | 10D | 8BS | 9RS | 8BS | 9BSR | 8BS | 8RS | 9.5BS | 2S | 9BS | 9BSR | 9.5RS |
| " | 2.0 + 1.0 | 10D | 3S | 10D | 7S | 9.5RSB | 9.5BS | 10D | 8BS | 9RS | 9BS | 1SB | 9.5BS | 9.5BS | 9.5RS |
| " | 2.0 + 2.0 | 10D | 3S | 10D | 8BS | 9.5BS | 10D | 10D | 9BSF | 9.5RS | 9.5BS | 4S | 9.5BS | 10D | 10N |
| " | 2.0 + 4.0 | 10D | 3BS | 10N | 10D | 10N | 10N | 10N | 9BSF | 9.5RS | 9.5BS | 3S | 9.5BS | 10D | 10N |
| Control | 0 | 0 | 0 | 0 | 0 | 0 | 0 | 0 | 0 | 0 | 0 | 0 | 0 | 0 | 0 |

TABLE XXII

COMBINATION OF 1-METHOXY-2,6-BIS(TRIFLUOROMETHYL)-1H-IMIDAZO(4,5-b)PYRIDINE ("A") + ATRAZINE ("B")

| Compounds | Rates Lbs./Acre | | Morning Glory | Corn | Foxtail Millet | Ragweed | Barnyard Grass | Large Crabgrass | Pigweed | Sorghum | Rice | Velvet Leaf | Corn | Jimson Weed | Johnson Grass | Lambs Quarter |
|---|---|---|---|---|---|---|---|---|---|---|---|---|---|---|---|---|
| A + B | 0.25 + | 0.25 | 3BS | 0 | 3B | 2S | 0 | 2S | 5SB | 0 | 2B | 2S | 0 | 2B | 0 | 7BS |
| " | 0.25 | 0.5 | 5BS | 0 | 4B | 8BS | 4S | 4SB | 6BS | 0 | 3B | 4SB | 2S | 8BS | 0 | 8BS |
| " | 0.25 | 1.0 | 10D | 0 | 7BS | 8BS | 3SB | 4SB | 8BS | 1B | 7B | 10D | 0 | 9BS | 1B | 8BS |
| " | 0.25 | 2.0 | 10D | 0 | 9BS | 10D | 8BS | 6BS | 8BS | 0 | 8B | 10D | 0 | 10D | 2B | 7BS |
| " | 0.5 + | 0.25 | 9BS | 0 | 3B | 4BS | 3SB | 6BS | 7SB | 0 | 5B | 4SB | 2S | 8BS | 0 | 6SB |
| " | 0.5 | 0.5 | 9BS | 0 | 4B | 6S | 4S | 4S | 6SB | 0 | 6B | 5SB | 0 | 10D | 2S | 7SB |
| " | 0.5 | 1.0 | 10D | 0 | 5BS | 10D | 4SB | 5SB | 7BS | 0 | 7B | 9BS | 0 | 10D | 0 | 7SB |
| " | 0.5 | 2.0 | 8BS | 4SB | 5BS | 10D | 7BS | 7BS | 8SB | 0 | 5B | 10D | 0 | 9BS | 2S | 7BS |
| " | 1.0 + | 0.25 | 9.5BS | 0 | 7BS | 4SB | 4S | 5SB | 3SB | 0 | 0 | 8BS | 0 | 9BS | 2S | 8BS |
| " | 1.0 | 0.5 | 10D | 0 | 7BS | 7SB | 4S | 5SB | 8SB | 1B | 3BS | 9.5BS | 0 | 9BS | 2S | 8BS |
| " | 1.0 | 1.0 | 9.5BS | 0 | 7BS | 8BS | 5SB | 5SB | 8SB | 1B | 5B | 10D | 1S | 9.5BS | 1S | 9SB |
| " | 1.0 | 2.0 | 10D | 0 | 9.5BS | 9SB | 8SB | 8SB | 8BS | 3SB | 8B | 9.5BS | 0 | 9.5BS | 2SB | 9BS |
| " | 2.0 + | 0.25 | 9.5BS | 0 | 8BS | 8BS | 5SB | 8BS | 8BS | 4B | 5B | 9BS | 0 | 9BS | 3BS | 8BS |
| " | 2.0 | 0.5 | 10D | 0 | 8BS | 9BS | 4B | 6BS | 8SB | 3BS | 5B | 9BS | 2S | 9BS | 4BS | 9BS |
| " | 2.0 + | 1.0 | 10D | 0 | 8BS | 10D | 5SB | 7BS | 8SB | 2B | 7B | 10D | 2S | 10D | 4SB | 8BS |
| " | 2.0 | 2.0 | 10D | 0 | 8BS | 10D | 8BS | 7BS | 8SB | 5B | 7B | 10D | 3S | 10D | 4B | 9BS |
| Control | 0 | | 0 | 0 | 0 | 0 | 0 | 0 | 0 | 0 | 0 | 0 | 0 | 0 | 0 | 0 |

EXAMPLES 108-110

1-Methoxy-6-chloro-2-trifluoromethyl-1H-imidazo(4,5-b)pyridine was evaluated separately in combination with each of alachlor, atrazine, and propachlor. The evaluations were conducted under field conditions at a location in the southern coastal plain. The compounds were formulated by tank-mixing a commercial application of the respective known herbicide with an emulsifiable concentrate of the 1-methoxy-6-chloro-2-trifluoromethyl-1H-imidazo(4,5b)pyridine. The tank-mixed formulation was then applied to the soil surface immediately after planting with corn. Prior to planting, the plots had been broadcast with foxtail millet (*Setaria italica*) and sicklepod (*Cassia obtusifolia*) and disced. However, additional weed seeds, including weed seeds of each of the named species, were present as a natural infestation of the plots. The growing conditions were typical for the area. Evaluations were made of corn injury and stand reduction, also of the control of the weed species. There were three replications per treatment pattern, and the ratings were averaged for the three replications. Results are given in the following table for stand reduction.

TABLE XXIV:

COMBINATION OF 1-METHOXY-6-CHLORO-2-TRIFLUOROMETHYL-1H-IMIDAZO(4,5-b)PYRIDINE ("A") ALACHLOR ("B"), ATRAZINE ("C"), AND PROPACHLOR ("D")

| Treatment | Rate in Lbs./Acre | Reduction in Emergence (10 Days) | Percent Corn Injury | | Percent Weed Control | | | | | |
|---|---|---|---|---|---|---|---|---|---|---|
| | | | | | Foxtail Millet | | | Sicklepod | | |
| | | | 23 Days | 64 Days | 16 Days | 24 Days | 42 Days | 16 Days | 24 Days | 42 Days |
| A | 1.0 | 0 | 0 | 3 | 61 | 88 | 90 | 14 | 14 | |
| " | 1.5 | 0 | 0 | 0 | 33 | 92 | 98 | 14 | 0 | ↑ |
| " | 2.0 | 9 | 13 | 17 | 11 | 100 | 100 | 0 | 0 | NO |
| " | 3.0 | 10 | 17 | 23 | 56 | 100 | 100 | 0 | 0 | |
| B | 2.0 | 3 | 0 | 0 | 67 | 62 | 97 | 0 | 0 | READING |
| A+B | 0.75+0.75 | 0 | 0 | 0 | 89 | 83 | 95 | 14 | 0 | |
| " | 0.75+1.0 | 2 | 0 | 0 | 100 | 96 | 98 | 14 | 57 | MADE |
| " | 1.0 +1.0 | 0 | 0 | 0 | 100 | 96 | 100 | 0 | 0 | ↓ |
| " | 1.0 +1.5 | 6 | 0 | 0 | 94 | 100 | 100 | 14 | 71 | |
| " | 1.5 +2.0 | 0 | 0 | 0 | 100 | 100 | 100 | 29 | 0 | |
| C | 2 | 4 | 0 | 7 | 11 | 33 | 88 | 0 | 57 | |
| A+C | 0.75+0.75 | 0 | 0 | 0 | 44 | 79 | 97 | 0 | 14 | |
| " | 0.75+1 | 0 | 0 | 3 | 44 | 79 | 98 | 0 | 14 | |
| " | 1 +1 | 0 | 0 | 0 | 72 | 96 | 100 | 29 | 43 | |
| " | 1 +1.5 | 0 | 0 | 0 | 61 | 96 | 100 | 57 | 86 | |
| " | 1.5 +2 | 0 | 0 | 7 | 50 | 100 | 100 | 43 | 86 | |
| D | 5 | 0 | 0 | 0 | 72 | 100 | 95 | 14 | 14 | |
| A+D | 0.75+2 | 10 | 0 | 7 | 100 | 92 | 97 | 0 | 0 | |
| " | 0.75+3 | 0 | 0 | 0 | 100 | 100 | 100 | 14 | 29 | |
| " | 1 +2 | 0 | 0 | 0 | 100 | 96 | 100 | 29 | 29 | |
| " | 1 +3 | 0 | 0 | 0 | 100 | 100 | 100 | 14 | 0 | |
| " | 1 +5 | 13 | 0 | 0 | 100 | 100 | 100 | 29 | 0 | |

The compounds of the present invention can also be employed as the starting materials in a reaction to prepare yet other compounds useful as herbicides. In general, this reaction comprises the treatment of one of the compounds of the present invention with a nucleophilic reagent; the reaction results in loss of the 1-OR$^3$ moiety and introduction of the nucleophilic ion into the pyridine ring, or in reduction. Suitable nucleophilic reagents are compounds containing an amine group, in the case of those present compounds which are ethers; and compounds containing a halide ion, in the case of those of the present compounds which are esters, including the carbamate and sulfonate esters. The overall reaction scheme can be summarized as follows:

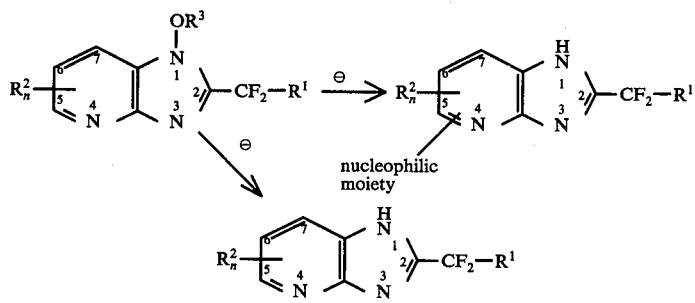

15

Rearrangement is the course of reaction except where a bromide or iodide is employed, in which case, reduction occurs. The introduced nucleophilic moiety locates at either the 5 or 7 positions, depending on the identity of $R^2$ and the nucleophilic moiety.

In the instance of either reduction or introduction of the nucleophile, the products are useful, in accordance with prior teachings, as herbicides. See U.S. Pat. No. 3,459,759.

Two synthetic routes are useful in the preparation of the starting 1-hydroxy compounds:

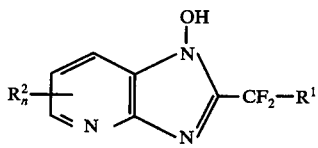

In a first synthetic route, the compounds are prepared by reduction of a precursor of the formula:

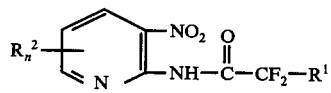

The reaction is believed to go through several intermediates which are not isolatable, but yields as product the desired 1-hydroxy-1H-imidazo(4,5-b)pyridine compound. The reaction conditions are not critical; however, it is generally preferred to employ as reducing agent two moles of hydrogen per mole of the nitropyridineamine, in the presence of a minor amount of a catalyst comprising a noble metal, preferably palladium. In a representative synthesis, 1-hydroxy-6-chloro-2-(trifluoromethyl)-1H-imidazo(4,5-b)pyridine was prepared as follows:

5-Chloro-3-nitro-2-(trifluoroacetamido)pyridine (2.0 grams) was hydrogenated with two moles of hydrogen in ethanol containing 0.5 gram of 5 percent palladium on carbon. The resulting reaction mixture was filtered and evaporated to separate the desired 6-chloro-1-hydroxy-2-(trifluoromethyl)-1H-imidazo(4,5-b)pyridine compound which, after recrystallization from benzene melted at 268°–70° C.

Analysis, Calc.: C, 35.39; H, 1.27; N, 17.69. Found: C, 35.59; H, 1.45; N, 17.77.

In a second synthetic route, a suitable 1-hydroxy compound

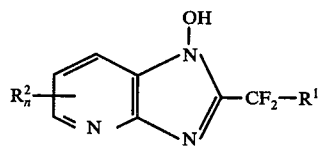

is itself utilized as a precursor to other 1-hydroxy compounds which serve as starting materials for the preparation of the compounds of the present invention. In this route, the initially employed 1-hydroxy compound is subjected to reactions to introduce onto the pyridine ring one or more desired groups and/or to convert one or more substituents already present on the pyridine ring to the desired group or groups.

Thus, for example, the 1-hydroxy compound can be halogenated or nitrated at a position or positions previously unsubstituted. A nitro group already present can be reduced to an amino group; and an amino group already present can also be oxidized back to a nitro group. An amino group can also be diazotized and replaced by, for example, a halo group, a nitrile group, or a loweralkylthio group. Oxidation of the loweralkylthio-substituted compound yields the corresponding loweralkylsulfonyl-substituted compound. The fluorinated groups ($R^2 = -CF_3$, $-CF_2Cl$, or $-CF_2H$) are readily obtained initially by conversion of a nitrile to a carboxyl group; subsequent treatment with $SF_4$ in the presence of HF yields the $-CF_3$ group. Alternately, conversion to an aldehyde and treatment with $SF_4$ alone yields the $-CF_2H$ group; and subsequent chlorination converts the $-CF_2H$ group to the corresponding $-CF_2Cl$ group. An alkyl substituent is introduced by reaction of an alkyl lithium with a halo-substituted 1-hydroxy compound; and a perfluoroalkyl substituent is introduced by reaction of a halo-substituted 1-hydroxy compound with a perfluoroalkyl iodide in the presence of copper. These and numerous other conversion substitution reactions are well known to those skilled in the art. Attention is directed to Fieser and Fieser, *Advanced Organic Chemistry* (Reinhold Publishing Corp., New York, N.Y., 1961), especially chapters 9 and 17. See also Wagner and Zook, *Synthetic Organic Chemistry* (John Wiley and Sons, Inc., New York, N.Y., 1953).

As will be understood by those skilled in the art, more than one of the foregoing reactions will be needed to complete the preparation of some of the compounds of the present invention; and in the case of all reactions, due consideration must be given to the orienting effect of substituent groups. Also, for those of the foregoing reactions which utilize a nucleophilic reagent, it may be necessary that the 1-hydroxy group first be converted to an ester or ether, as discussed hereinabove; and the reaction with nucleophilic reagent then conducted.

Preferred compounds of the present invention are those which are monosubstituted (n = 1) and the substituent ($R^2$) is halogen, nitro, —$CF_3$, —$CF_2Cl$, —$CF_2H$, or loweralkylsulfonyl of $C_1$-$C_4$.

A particularly preferred sub-genus of the compounds of the present invention is defined as follows:

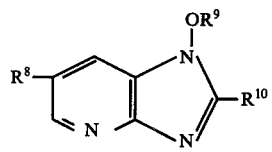

wherein $R^8$ represents halo or —$CF_3$; $R^9$ represents loweralkyl of $C_1$-$C_4$, loweralkenyl of $C_2$-$C_4$, benzyl, loweralkanoyl of $C_2$-$C_4$, loweralkenoyl of $C_3$-$C_4$, benzoyl, loweralkylsulfonyl of $C_1$-$C_4$, or carbamoyl of the formula

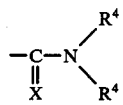

wherein X represents oxygen or sulfur, and one $R^4$ represents phenyl, loweralkyl of $C_1$-$C_4$, or loweralkenyl of $C_2$-$C_4$, and the other $R^4$ represents hydrogen, loweralkyl of $C_1$-$C_4$, or loweralkenyl of $C_2$-$C_4$, subject to the limitation that both $R^4$ moieties taken together do not contain more than six carbon atoms, or both $R^4$ moieties taken together represent straight-chain alkylene of $C_2$-$C_6$, both inclusive; and $R^{10}$ represents trifluoromethyl, pentafluoroethyl, or 1,1,2,2-tetrafluoroethyl.

I claim:

1. The method which comprises applying to a plant part a growth-inhibiting amount of an active agent, said active agent being a compound of the formula:

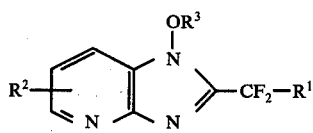

wherein $R^1$ represents hydrogen, chlorine, fluorine, difluoromethyl, perfluoroalkyl of $C_1$-$C_6$, or radical of the formula:

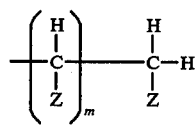

wherein each Z independently represents hydrogen or halogen and m represents 0 or 1; $R^2$ represents halogen, nitro, —$CF_3$, —$CF_2Cl$, —$CF_2H$, or loweralkylsulfonyl of $C_1$-$C_4$; and $R^3$ represents
(1) alkanoyl of $C_2$-$C_{16}$;
(2) alkenoyl of $C_3$-$C_{16}$;
(3) carbamoyl of the formula

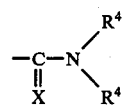

wherein X represents oxygen or sulfur; and one $R^4$ represents phenyl, loweralkyl of $C_1$-$C_4$, or loweralkenyl of $C_2$-$C_4$, and the other $R^4$ represents hydrogen, loweralkyl of $C_1$-$C_4$, or loweralkenyl of $C_2$-$C_4$, subject to the limitation that both $R^4$ moieties taken together do not contain more than six carbon atoms, or both $R^4$ moieties taken together represent straight-chain alkylene of $C_2$-$C_6$, both inclusive;
(4) radical of the formulae

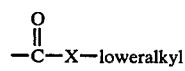

of $C_1$-$C_4$ or

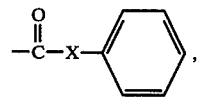

wherein X is, as above, oxygen or sulfur;
(5) radical of the formula

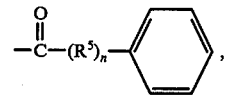

wherein $R^5$ represents methylene, ethylene, or vinylene, and n represents 0 or 1;
(6) radical of the formulae

and

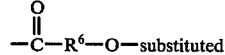

phenyl, wherein substituted phenyl is a phenyl radical bearing from 1-3 substituents, each of which is independently amino, nitro, chloro, methyl, or methoxy, and $R^6$ represents loweralkylene of $C_1$-$C_4$, both inclusive; or
(7) —$SO_2$—$R_7$ wherein $R^7$ is loweralkyl as above defined, cycloalkyl of $C_5$-$C_6$, phenyl, substituted phenyl as above defined, or benzyl.

2. The method of claim 1 wherein the active agent is 1-acetoxy-6chloro-2-(trifluoromethyl)-1H-imidazo(4,5-b)pyridine.

3. The method of claim 1 wherein the active agent is 1-octanoyloxy-6-chloro-2-(trifluoromethyl)-1H-imidazo(4,5-b)pyridine.

4. The method of claim 1 wherein the active agent is 1-(allylcarbamoyloxy)-6-chloro-2-(trifluoromethyl)1H-imidazo(4,5-b)pyridine.

5. The method of claim 1 wherein the active agent is 1-(methylsulfonyloxy)-6-chloro-2(trifluoromethyl)-1H-imidazo(4,5-b)pyridine.

6. The method of claim 1 wherein the active agent is 1-(methylcarbamoyloxy)-6-chloro-2-(trifluoromethyl)-1H-imidazo(4,5-b)pyridine.

7. The method of claim 1 wherein the active agent is 1-(2-methoxy-3,6-dichlorobenzoyloxy)-6-chloro-2-(trifluoromethyl)-1H-imidazo(4,5-b)pyridine.

8. The composition which comprises a surface active agent and a plant growth-inhibiting amount of an active agent which is a compound of the formula:

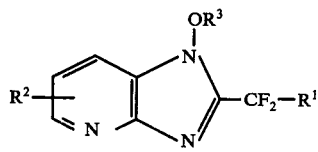

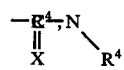

wherein $R^1$ represents hydrogen, chlorine, fluorine, difluoromethyl, perfluoroalkyl of $C_1$-$C_6$, or radical of the formula:

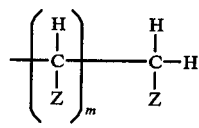

wherein each Z independently represents hydrogen or halogen and m represents 0 or 1; $R^2$ represents halogen, nitro, $-CF_3$, $-CF_2Cl$, $-CF_2H$, or loweralkylsulfonyl of $C_1$-$C_4$; and $R^3$ represents (1) alkanoyl of $C_2$-$C_{16}$;
(2) alkenoyl of $C_3$-$C_{16}$;
(3) carbamoyl of the formula

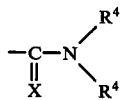

wherein X represents oxygen or sulfur; and one $R^4$ represents phenyl, loweralkyl of $C_1$-$C_4$, or loweralkenyl of $C_2$-$C_4$, and the other $R^4$ represents hydrogen, loweralkyl of $C_1$-$C_4$, or loweralkenyl of $C_2$-$C_4$, subject to the limitation that both $R^4$ moieties taken together do not contain more than six carbon atoms, or both $R^4$ moieties taken together represent straight-chain alkylene of $C_2$-$C_6$, both inclusive;

(4) radical of the formulae

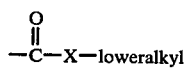

of $C_1$-$C_4$ or

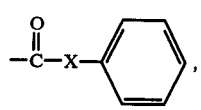

wherein X is, as above, oxygen or sulfur;

(5) radical of the formula

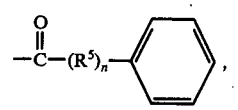

wherein $R^5$ represents methylene, ethylene, or vinylene, and n represents 0 or 1;

(6) radical of the formulae

and

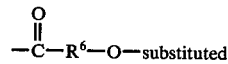

phenyl, wherein substituted phenyl is a phenyl radical bearing from 1-3 substituents, each of which is independently amino, nitro, chloro, methyl, or methoxy, and $R^6$ represents loweralkylene of $C_1$-$C_4$, both inclusive; or (7) $-SO_2-R^7$ wherein $R^7$ is loweralkyl as above defined, cycloalkyl of $C_5$-$C_6$, phenyl, substituted phenyl as above defined, or benzyl.

9. The composition of claim 8 wherein the active agent is 1-acetoxy-6-chloro-2-(trifluoromethyl)-1H-imidazo(4,5-b)pyridine.

10. The composition of claim 8 wherein the active agent is 1-octanoyloxy-6-chloro-2-(trifluoromethyl)-1H-imidazo(4,5-b)pyridine.

11. The composition of claim 8 wherein the active agent is 1-(allylcarbamoyloxy)-6-chloro-2-(trifluoromethyl)-1H-imidazo(4,5-b)pyridine.

12. The composition of claim 8 wherein the active agent is 1-(methylsulfonyloxy)-6-chloro-2-(trifluoromethyl)-1H-imidazo(4,5-b)pyridine.

13. The composition of claim 8 wherein the active agent is 1-(methylcarbamoyloxy)-6-chloro-2-(trifluoromethyl)-1H-imidazo(4,5-b)pyridine.

14. The composition of claim 8 wherein the active agent is 1-(2-methoxy-3,6-dichlorobenzoyloxy)-6-chloro-2-(trifluoromethyl)-1H-imidazo(4,5-b)pyridine.

15. The composition which comprises an inert finely divided solid and a plant growth inhibiting amount of an active agent which is a compound of the formula:

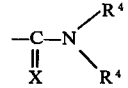

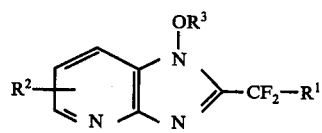

wherein $R^1$ represents hydrogen, chlorine, fluorine, difluoromethyl, perfluoroalkyl of $C_1$-$C_6$, or radical of the formula:

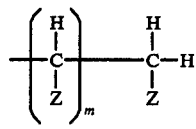

wherein each Z independently represents hydrogen or halogen and m represents 0 or 1; $R^2$ represents halogen, nitro, $-CF_3$, $-CF_2Cl$, $-CF_2H$, or loweralkylsulfonyl of $C_1$-$C_4$; and $R^3$ represents
(1) alkanoyl of $C_2$-$C_{16}$;
(2) alkenoyl of $C_3$-$C_{16}$;
(3) carbamoyl of the formula

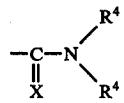

wherein X represents oxygen or sulfur; and one $R^4$ represents phenyl, loweralkyl of $C_1$-$C_4$, or loweralkenyl of $C_2$-$C_4$, and the other $R^4$ represents hydrogen, loweralkyl of $C_1$-$C_4$, or loweralkenyl of $C_2$-$C_4$, subject to the limitation that both $R^4$ moieties taken together do not contain more than six carbon atoms, or both $R^4$ moieties taken together represent straight-chain alkylene of $C_2$-$C_6$, both inclusive;
(4) radical of the formulae

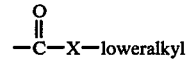

of $C_1$-$C_4$ or

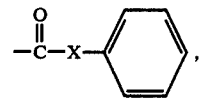

wherein X is, as above, oxygen or sulfur;
(5) radical of the formula

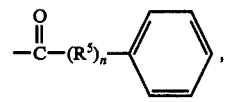

wherein $R^5$ represents methylene, ethylene, or vinylene, and n represents 0 or 1;
(6) radical of the formulae

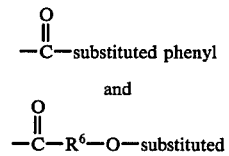

phenyl, wherein substituted phenyl is a phenyl radical bearing from 1–3 substituents, each of which is independently amino, nitro, chloro, methyl, or methoxy, and $R^6$ represents loweralkylene of $C_1$-$C_4$, both inclusive; or
(7) $-SO_2-R^7$ wherein $R^7$ is loweralkyl as above defined, cycloalkyl of $C_5$-$C_6$, phenyl, substituted phenyl as above defined, or benzyl.

* * * * *

UNITED STATES PATENT AND TRADEMARK OFFICE
CERTIFICATE OF CORRECTION

PATENT NO. : 4,082,534
DATED : April 4, 1978
INVENTOR(S) : George O. P. Doherty

It is certified that error appears in the above-identified patent and that said Letters Patent are hereby corrected as shown below:

In Column 39, lines 20-22, the structure

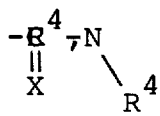

should be deleted.

In Column 40, lines 54-57, the structure

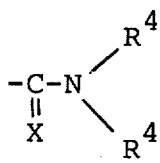

should be deleted.

Signed and Sealed this

Thirty-first Day of July 1979

[SEAL]

Attest:

Attesting Officer

LUTRELLE F. PARKER
*Acting Commissioner of Patents and Trademarks*